United States Patent
Dupuy et al.

(10) Patent No.: US 10,070,907 B2
(45) Date of Patent: Sep. 11, 2018

(54) ANGLED NOZZLE WITH CONNECTION ASSEMBLY SYSTEM

(71) Applicant: Biomet SAS, Valence (FR)

(72) Inventors: Alexis Dupuy, Sancourt (FR); Sebastien Chaligne, Brette les Pins (FR); Julie Mottet, Chabeuil (FR); Lenaic Giffard, Saint Genis Laval (FR)

(73) Assignee: Biomet SAS (FR)

( * ) Notice: Subject to any disclaimer, the term of this patent is extended or adjusted under 35 U.S.C. 154(b) by 655 days.

(21) Appl. No.: 14/638,664

(22) Filed: Mar. 4, 2015

(65) Prior Publication Data

US 2016/0256210 A1    Sep. 8, 2016

(51) Int. Cl.
*A61B 17/88* (2006.01)

(52) U.S. Cl.
CPC ...... *A61B 17/8811* (2013.01); *A61B 17/8816* (2013.01)

(58) Field of Classification Search
CPC ............... A61F 2/4601; A61B 17/8805; A61B 17/18808; A61B 17/8822; A61B 17/8811
See application file for complete search history.

(56) References Cited

U.S. PATENT DOCUMENTS

| | | |
|---|---|---|
| 2,047,378 A | 7/1936 | Martin |
| 4,466,435 A | 8/1984 | Murray |
| 4,619,613 A | 10/1986 | Dragan |
| 4,682,950 A | 7/1987 | Dragan |
| 4,769,011 A * | 9/1988 | Swaniger ............ A61F 2/4601 604/218 |
| 4,815,454 A | 3/1989 | Dozier, Jr. |
| D309,205 S | 7/1990 | Schuster |
| 5,000,361 A | 3/1991 | Briddell et al. |
| 5,033,951 A | 7/1991 | Cook |
| 5,222,821 A | 6/1993 | Osborne et al. |
| 5,370,221 A | 12/1994 | Magnusson et al. |
| D359,148 S | 6/1995 | Henrie |
| 5,741,265 A | 4/1998 | Chan |
| 5,788,104 A | 8/1998 | Hoyt |
| 6,190,392 B1 | 2/2001 | Vandewalle et al. |

(Continued)

FOREIGN PATENT DOCUMENTS

| | | |
|---|---|---|
| CN | 107592801 A | 1/2018 |
| DE | 9319325 U1 | 2/1994 |

(Continued)

OTHER PUBLICATIONS

Biomet "Different Solutions—Great Results" brochure, 8 pages, 2010.

(Continued)

*Primary Examiner* — Jason-Dennis Stewart
(74) *Attorney, Agent, or Firm* — Schwegman Lundberg & Woessner, P.A.

(57) ABSTRACT

An apparatus for bone cement delivery comprising, a proximal nozzle having a proximal end configured to couple to a bone cement source and a first distal delivery end having a circular cross section, a distal nozzle having a proximal end configured to slideably couple to the first distal delivery end and a second distal delivery end having an oblong cross section, that can be slanted, and an attachment mechanism configured to slideably retain the distal nozzle to the proximal nozzle.

14 Claims, 16 Drawing Sheets

(56) References Cited

U.S. PATENT DOCUMENTS

| | | | |
|---|---|---|---|
| 6,502,608 B1* | 1/2003 | Burchett | A61B 17/8816 141/383 |
| D711,530 S | 8/2014 | Gleason, Jr. et al. | |
| 2007/0016216 A1 | 1/2007 | Tague et al. | |
| 2008/0065088 A1* | 3/2008 | Hughes | B01F 5/0685 606/93 |
| 2009/0137946 A1 | 5/2009 | Nassiri et al. | |
| 2010/0010495 A1* | 1/2010 | Foster | A61B 17/8833 606/93 |
| 2010/0256646 A1* | 10/2010 | Pinal | A61B 17/00491 606/92 |
| 2010/0276458 A1 | 11/2010 | Buck | |
| 2013/0158560 A1 | 6/2013 | Gleason et al. | |
| 2014/0023987 A1 | 1/2014 | Cardon | |

FOREIGN PATENT DOCUMENTS

| | | |
|---|---|---|
| DE | 10005105 A1 | 8/2001 |
| DE | 20120080 U1 | 4/2003 |
| EP | 1749586 A1 | 2/2007 |
| JP | 2018508332 | 3/2018 |
| WO | WO-0069360 A1 | 11/2000 |
| WO | WO-0126824 A1 | 4/2001 |
| WO | WO-2007024641 A2 | 3/2007 |
| WO | WO-2016139538 A1 | 9/2016 |

OTHER PUBLICATIONS

Biomet Optivac Vacuum Mixing System Brochure, 2 pages, Jan. 1, 1996.
Biomet Optivac® Kits for the US Market, 4 pages.
Biomet Optivac® Vacuum Mixing System retrieved from URL www.biomet.com/orthopedics/productDetail.cfm?category=7&product=224 on Jan. 30, 2012, 1 page.
German Search Report dated Oct. 5, 2012 for German patent Application No. 202012002829.4 filed Mar. 21, 2012 claiming benefit of U.S. Appl. No. 13/417,599, filed Mar. 12, 2012.
Great Results Optipac, Optivac and Biomet Bone Cements retrieved from URL www.bonecement.com/home on Jan. 30, 2012, 1 page.
Hip Acetabular Pressurization Biomet Cement and Cementing Systems retrieved from URL www.bonecement.com/products/pressurization/hip-acetabular on Jan. 30, 2012, 1 page.
Hip Femoral Pressurization Biomet Cement and Cementing Systems retrieved from URL www.bonecement.com/products/pressurization/hip-femoral on Jan. 30, 2012, 2 pages.
Knee Pressurization Biomet Cement and Cementing Systems retrieved from URL www.bonecement.com/products/pressurization/knee/ on Jan. 30, 2012, 1 page.
Optipac® Biomet product listing, 2 pages, 2005.
Optivac® Kits for the US Market, Biomet, 4 pages, 2005.
"International Application Serial No. PCT/IB2016/000383, International Preliminary Report on Patentability dated Sep. 14, 2017", 9 PGS.
"International Application Serial No. PCT/IB2016/000383, International Search Report dated Jul. 7, 2016", 6 pgs.
"International Application Serial No. PCT/IB2016/000383, Written Opinion dated Jul. 7, 2016", 7 pgs.
"European Application Serial No. 16715088.7, Response filed Apr. 13, 2018 to Office Action dated Oct. 20, 2018.", 13 pgs.

* cited by examiner

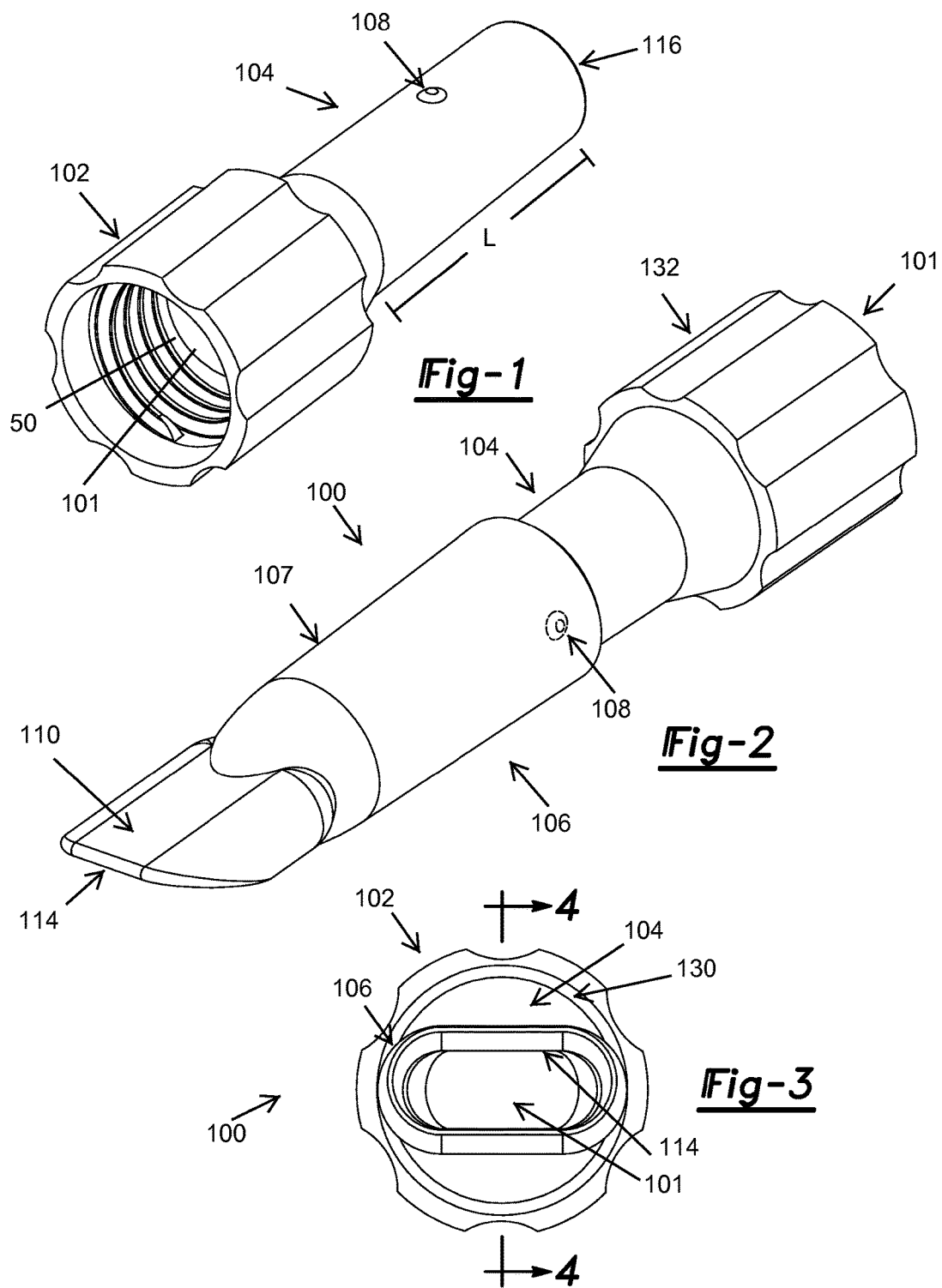

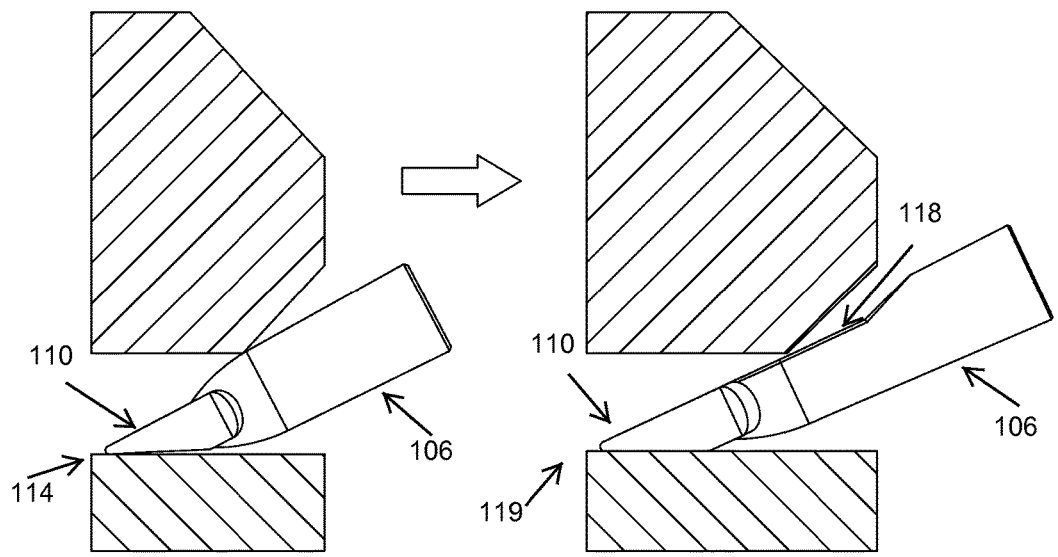
*Fig-11A*  *Fig-11B*
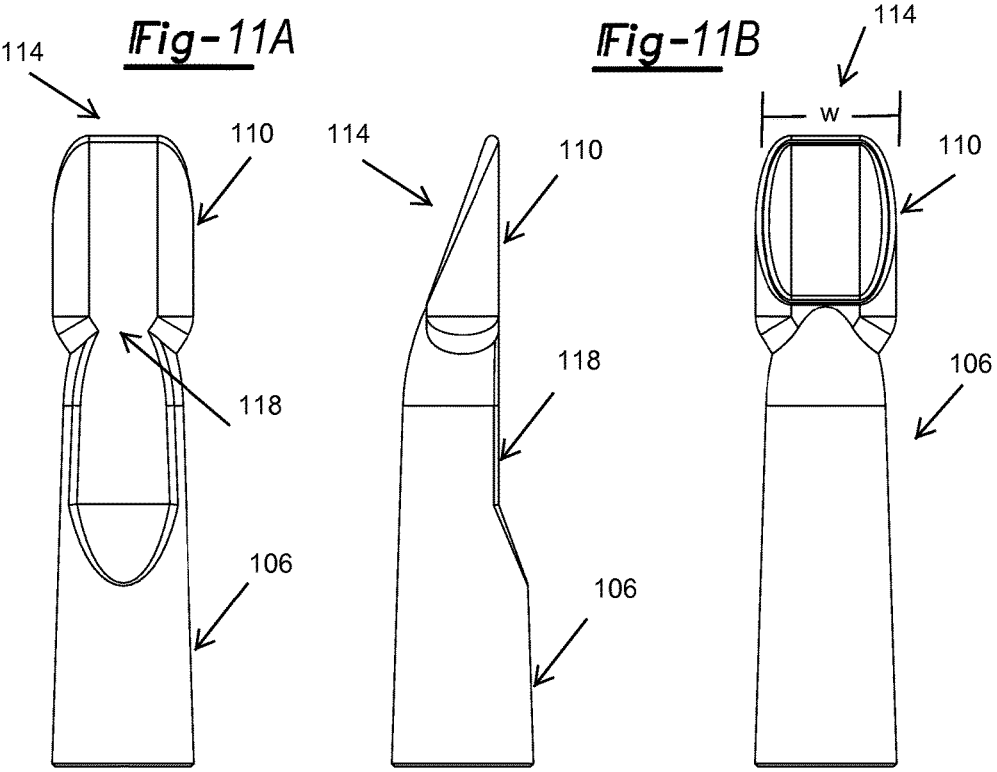
*Fig-12*  *Fig-13*  *Fig-14*

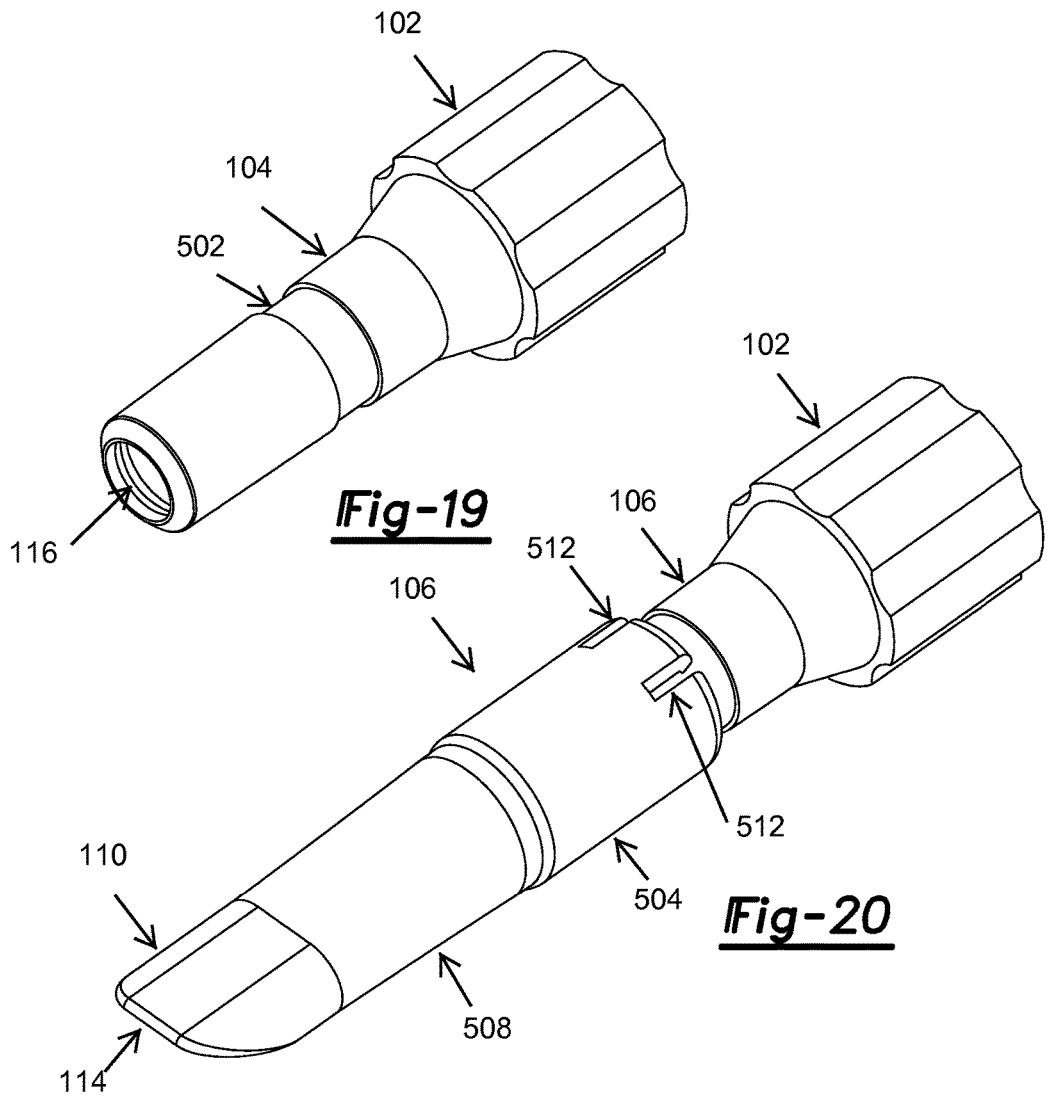
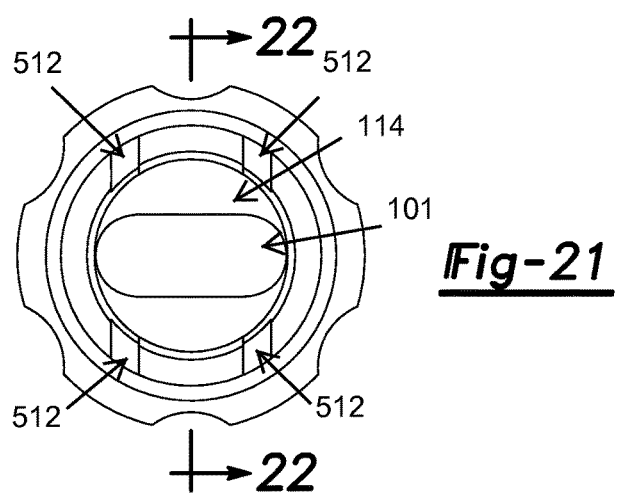

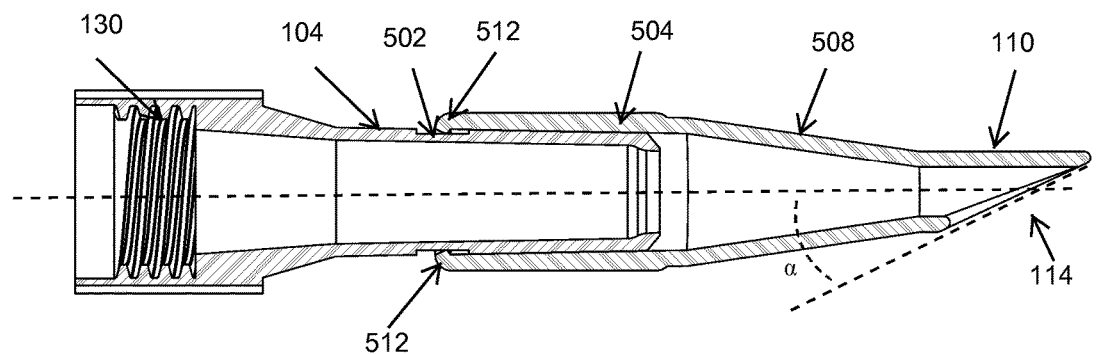
*Fig-22*
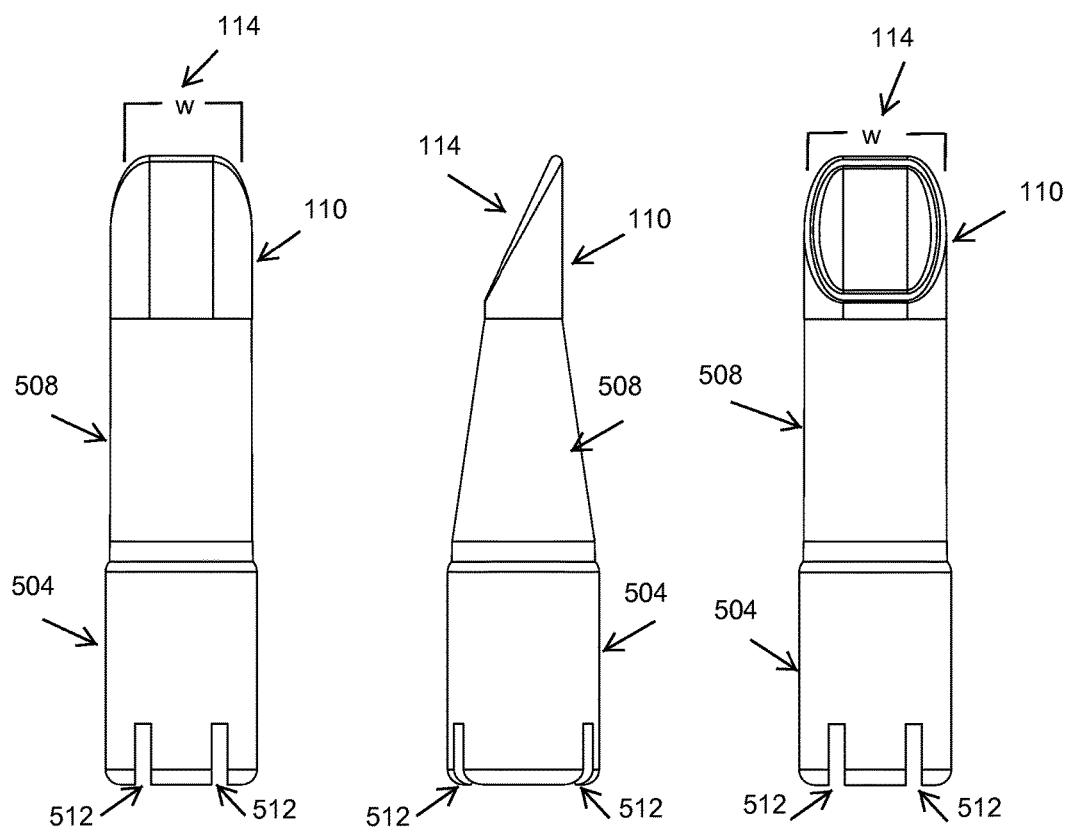
*Fig-23*  *Fig-24*  *Fig-25*

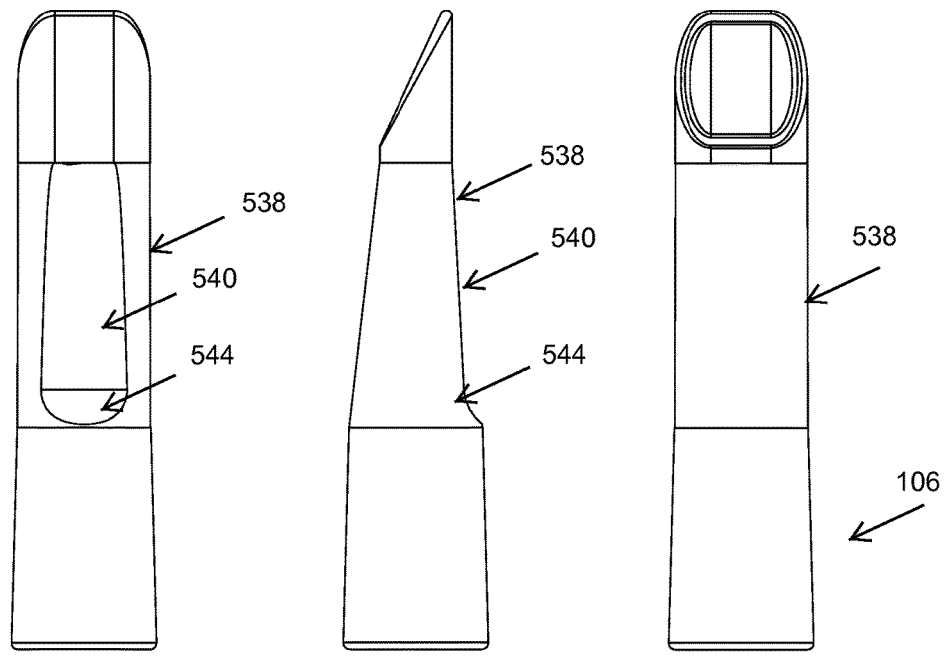
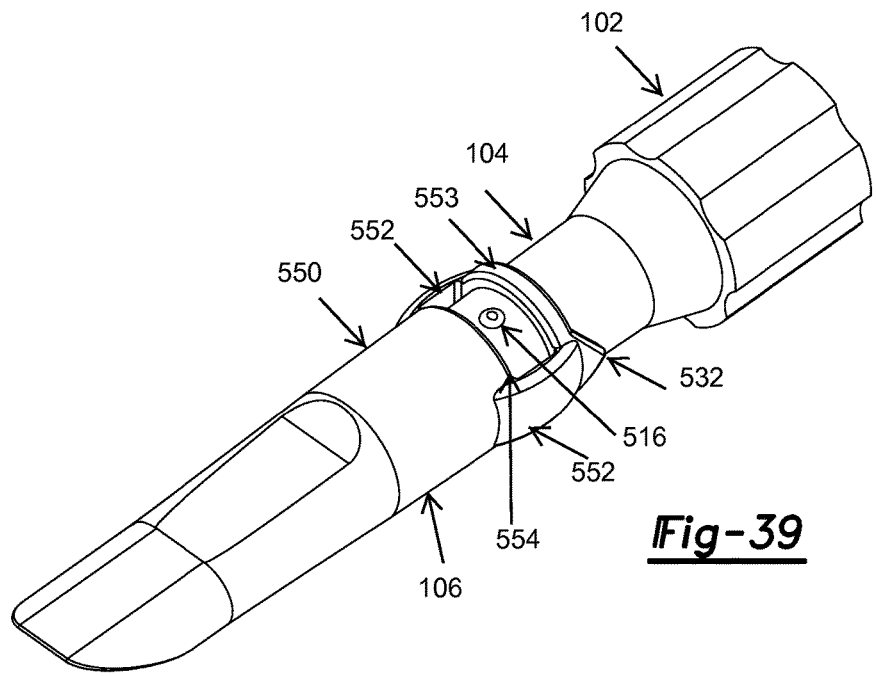

ANGLED NOZZLE WITH CONNECTION ASSEMBLY SYSTEM

FIELD

The present disclosure relates to a bone cement apparatus and associated method for applying and delivering bone cement.

INTRODUCTION

This section provides background information related to the present disclosure which is not necessarily prior art.

In various orthopedic applications, including knee, hip, shoulder, or other arthroplasty, bone cement can be used to anchor and stabilize an implant relative to a corresponding bone. Bone cement can be prepared in a mixer or in a mixer integrated with a bone cement cartridge. The cartridge can be attached to a bone cement nozzle and delivered using a bone cement gun or other bone cement applicator.

SUMMARY

This section provides a general summary of the disclosure, and is not a comprehensive disclosure of its full scope or all of its features.

The present teachings provide an apparatus for bone cement delivery includes, a proximal nozzle portion having a proximal end configured to couple to a bone cement source and a first distal delivery end having a circular cross section, a distal nozzle augment having a proximal end configured to slideably couple to the first distal delivery end and a second distal delivery end having an oblong cross section, and an attachment mechanism configured to slideably retain the distal nozzle augment to the proximal nozzle portion.

In another embodiment, an apparatus for bone cement delivery includes, a proximal nozzle portion extending along a first longitudinal axis and having a proximal end configured to couple to a bone cement source and a first distal delivery end having a circular cross section perpendicular to the first longitudinal axis, a distal nozzle augment extending along a second longitudinal axis and having a proximal end configured to slideably couple to the first distal delivery end and a second distal delivery end having an oblong cross section, the second distal delivery end having a slanted face disposed at an acute angle relative to the second longitudinal axis, a clearance portion disposed on the distal nozzle augment opposite the slanted face, and an attachment mechanism configured to slideably retain the distal nozzle augment to the proximal nozzle portion.

In yet another embodiment, a method for bone cement delivery includes coupling a proximal end of a first nozzle portion to a bone cement source, expelling flat layers of bone cement out an oblong distal opening of a second nozzle portion slideably coupled to the first nozzle portion, slideably removing the second nozzle portion from the first nozzle portion to expose a circular distal opening of the first nozzle portion, and expelling bone cement out of the circular distal opening of the first nozzle portion.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a bone cement nozzle according to the present teachings;

FIG. 2 is a perspective view of a nozzle augment attached to the bone cement nozzle of FIG. 1;

FIG. 3 is a rear end view of the bone cement nozzle and nozzle augment of FIG. 2;

Figure 8:
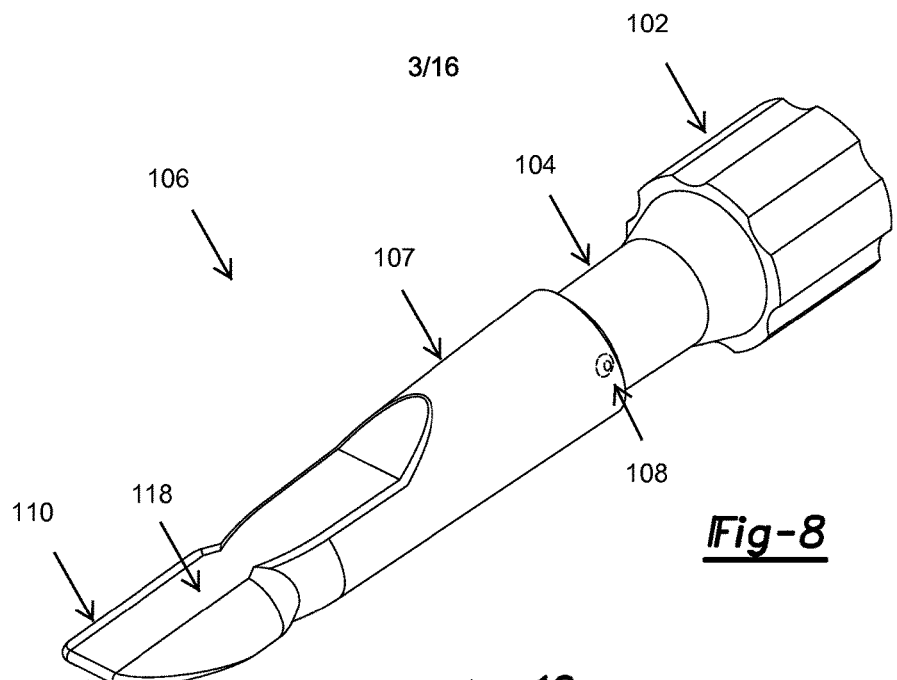
FIG. 8 is an alternative nozzle augment attached to the bone nozzle of FIG. 1.
Figure 9:
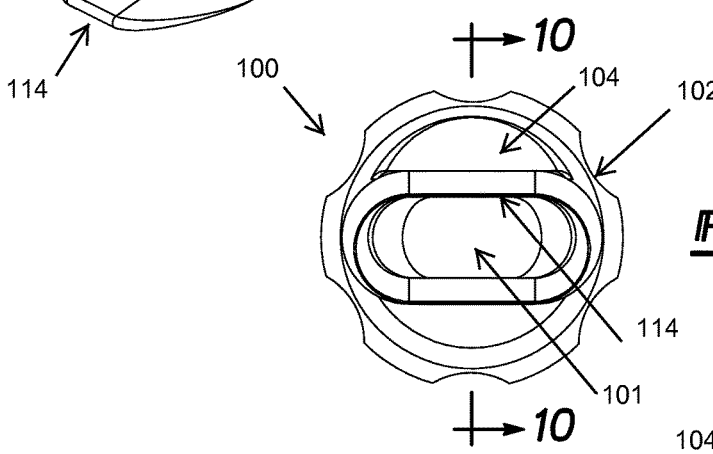
Figure 10:
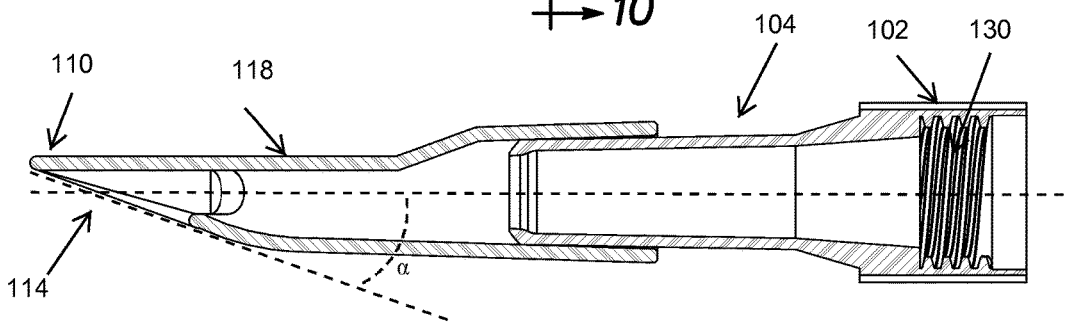
Figure 15:
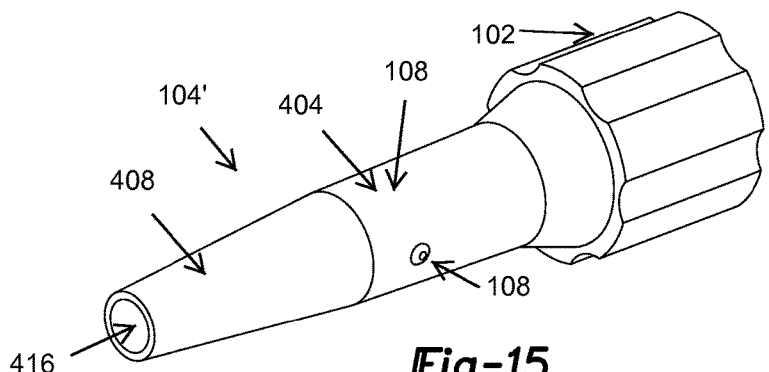
Figure 16:
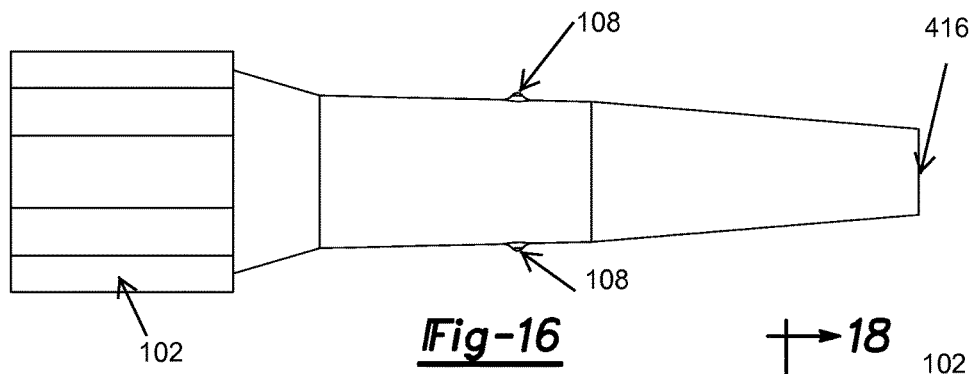
Figure 17:
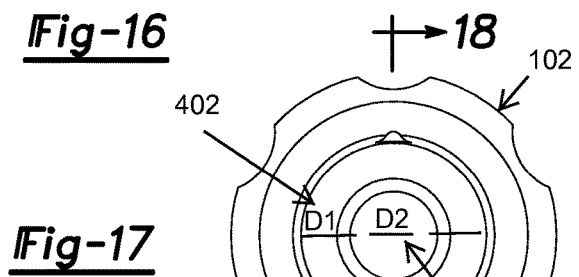
Figure 18:
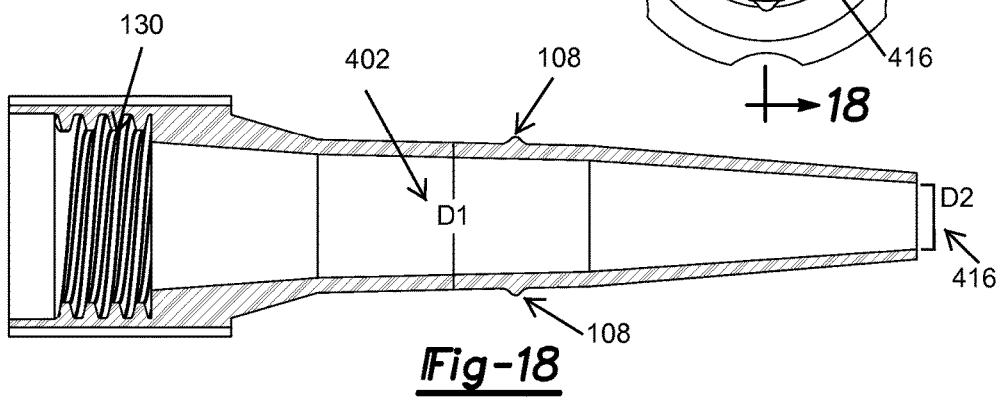
Figure 26:
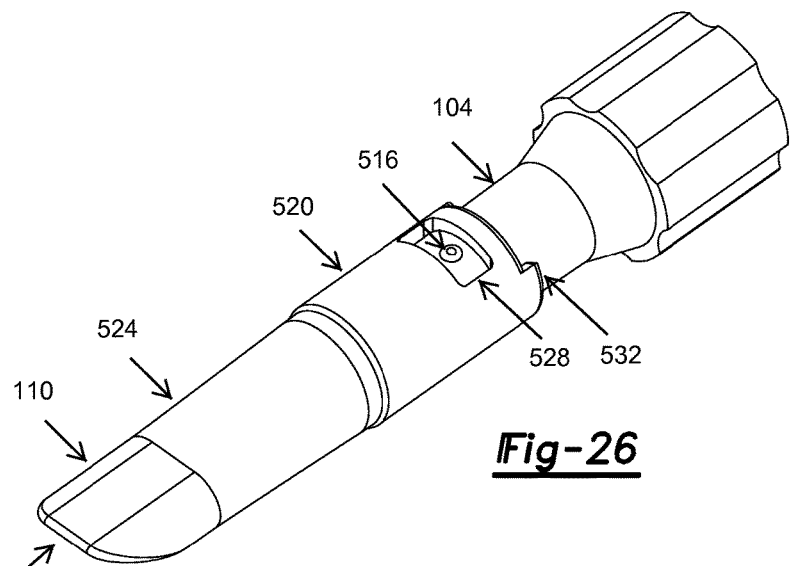
Figure 27:
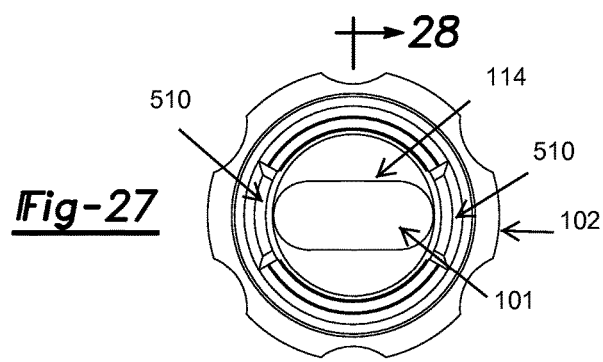
Figure 28:
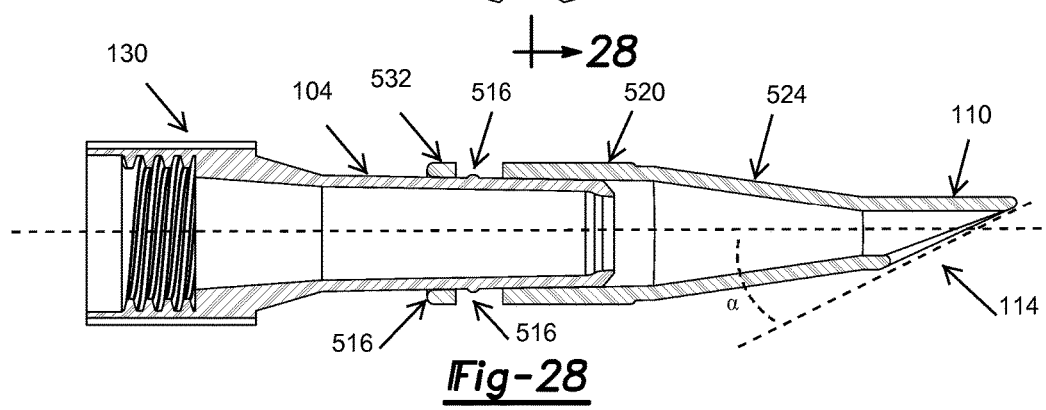
Figure 29:
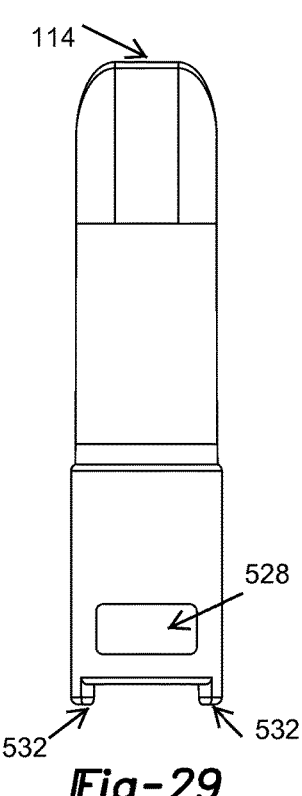
Figure 30:
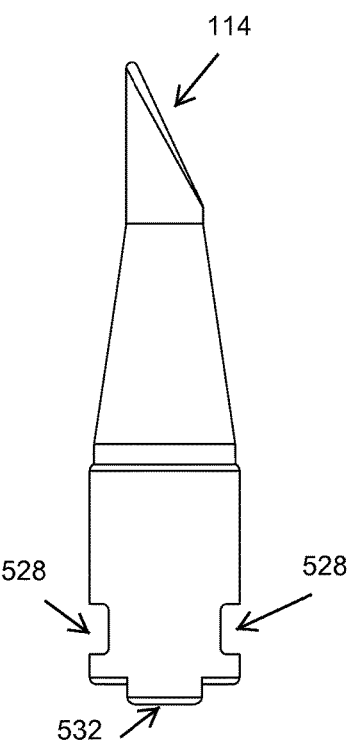
Figure 31:
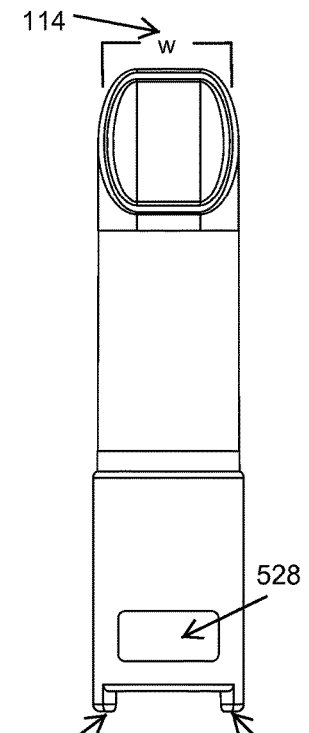
Figure 32:
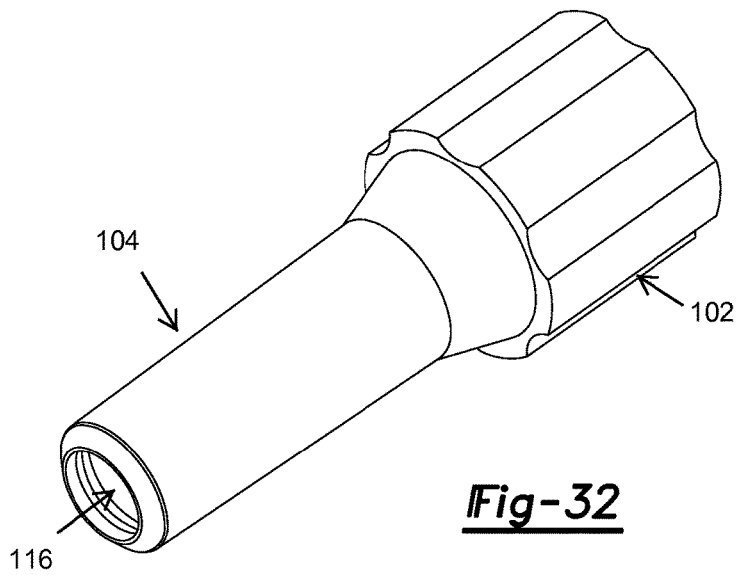
Figure 33:
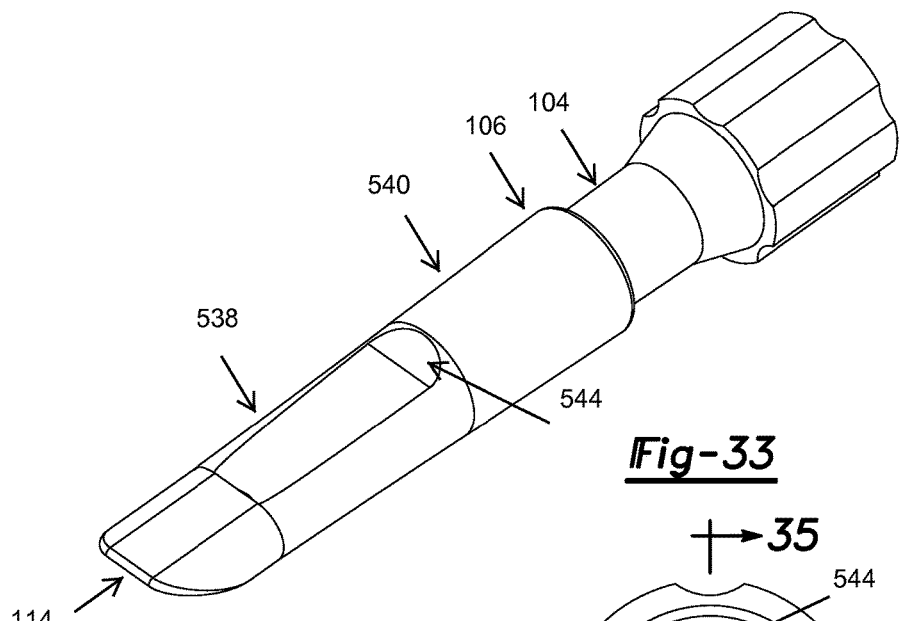
Figure 34:
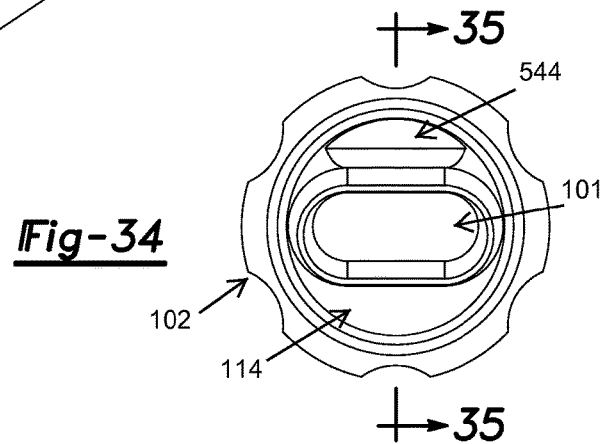
Figure 35:
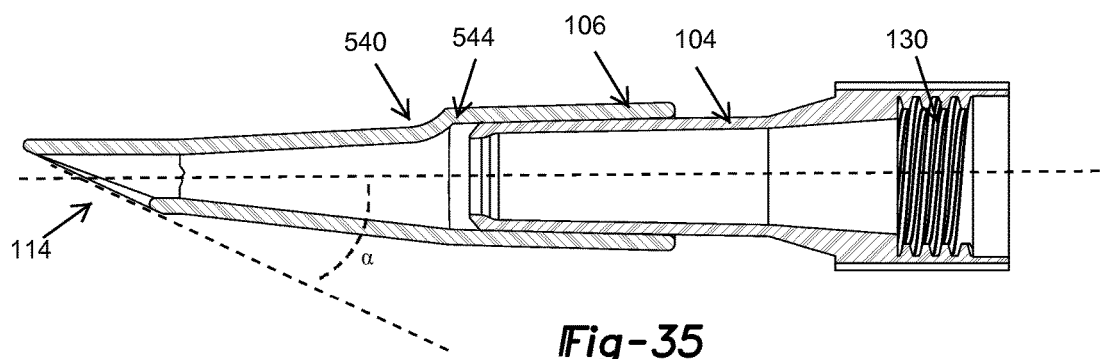
Figure 40:
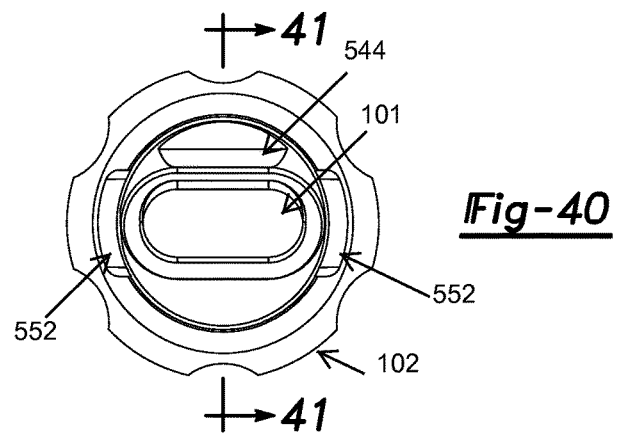
Figure 41:
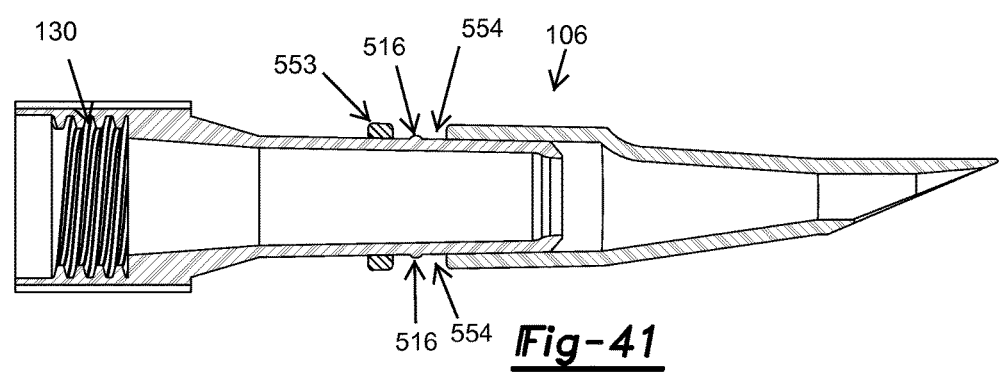
Figure 42:
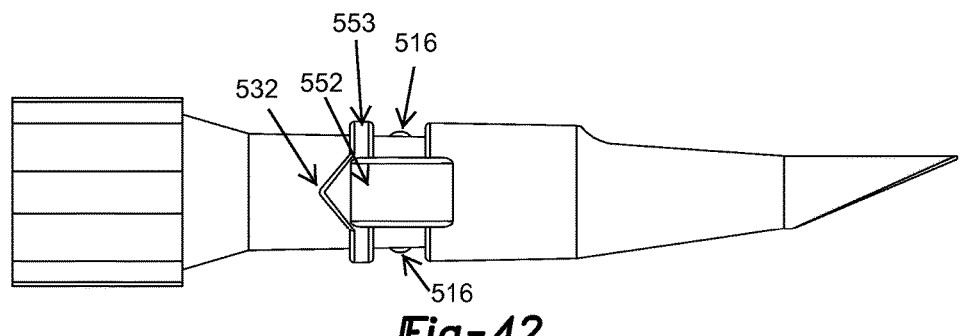
Figure 43:
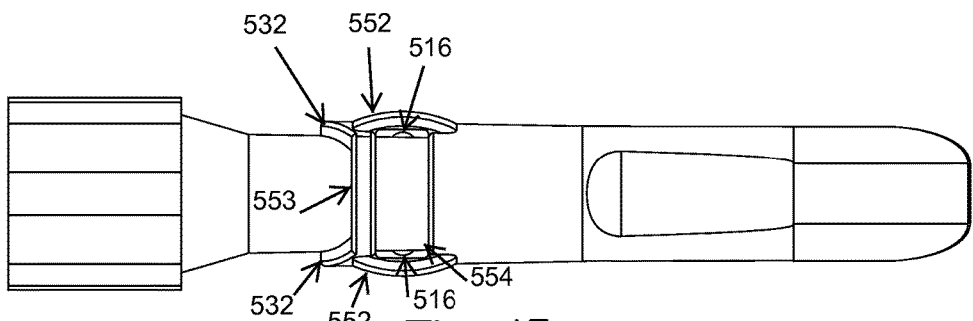
Figure 44:
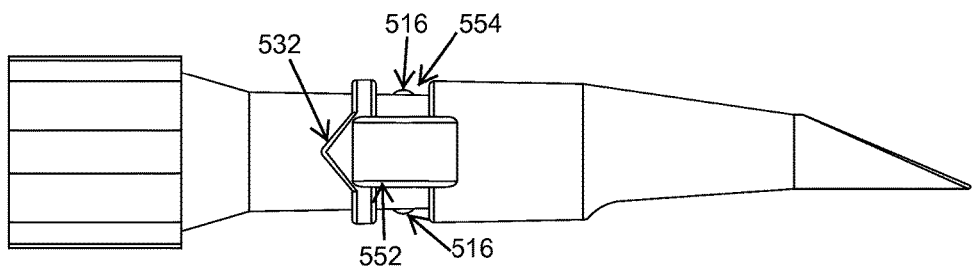
Figure 45:
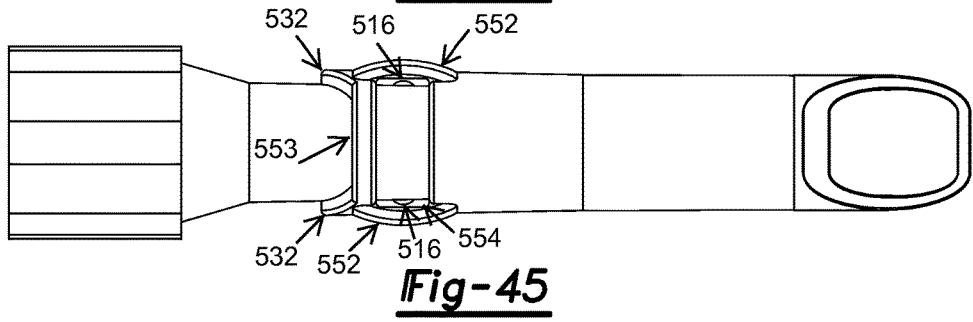
Figure 46:
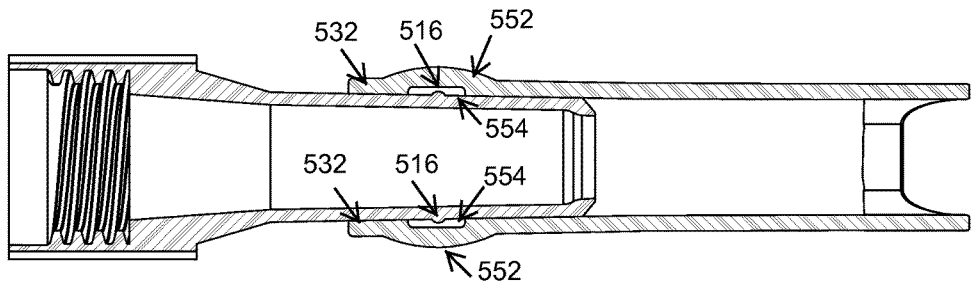
Figure 47:
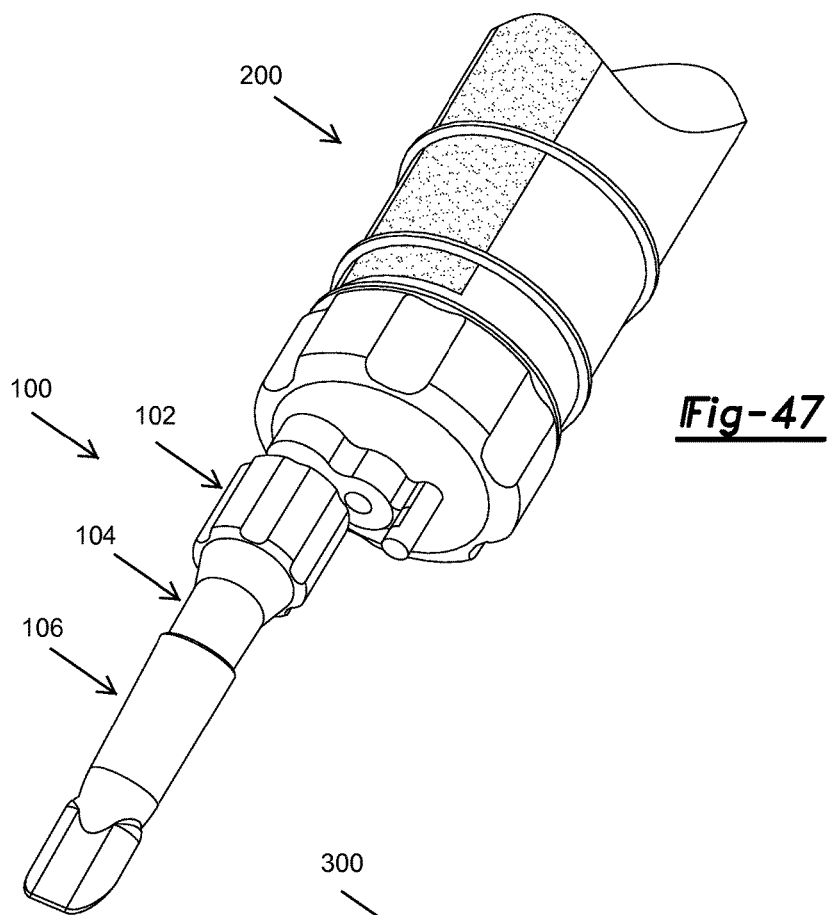
Figure 48:
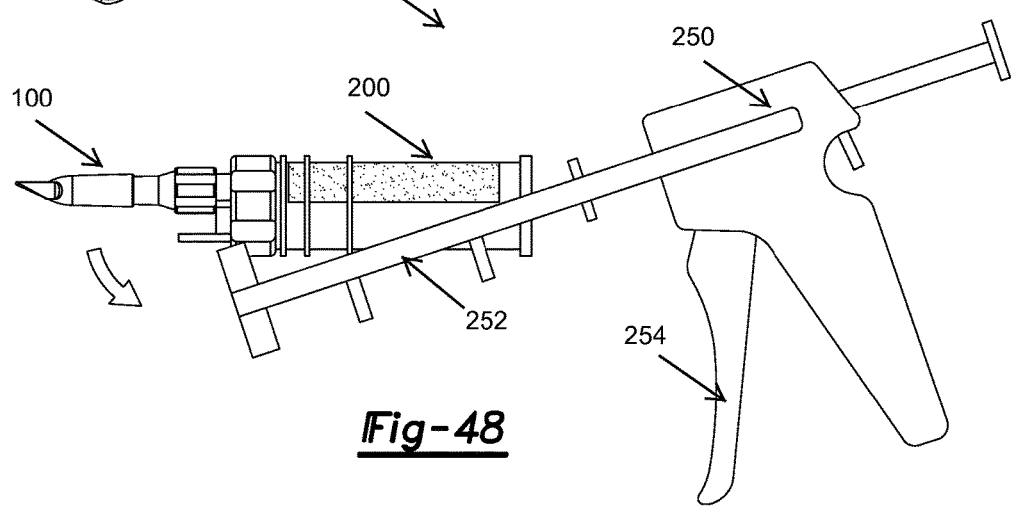
Figure 49:
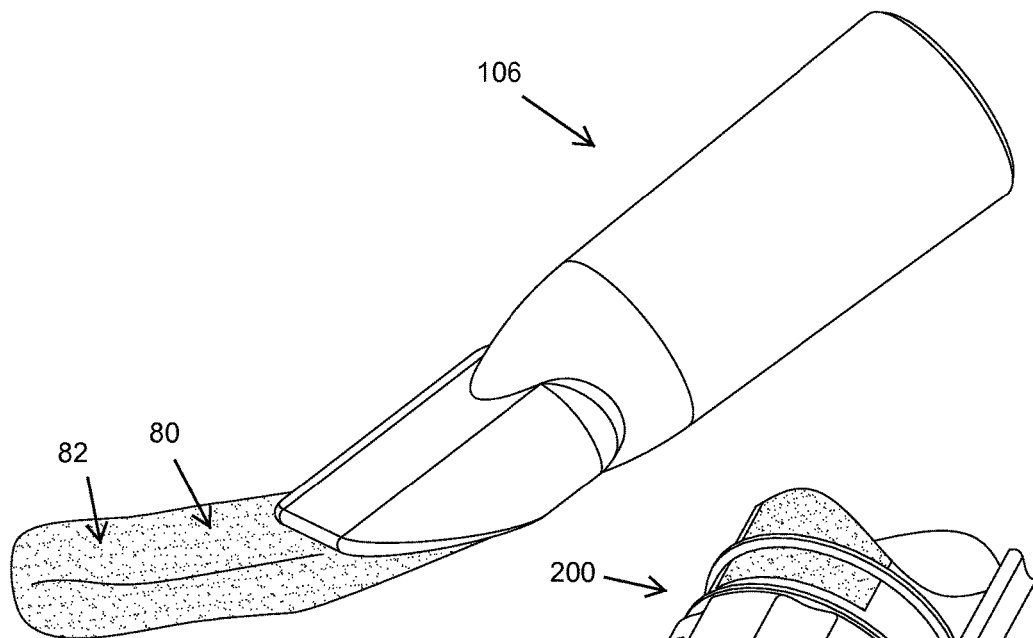
Figure 50:
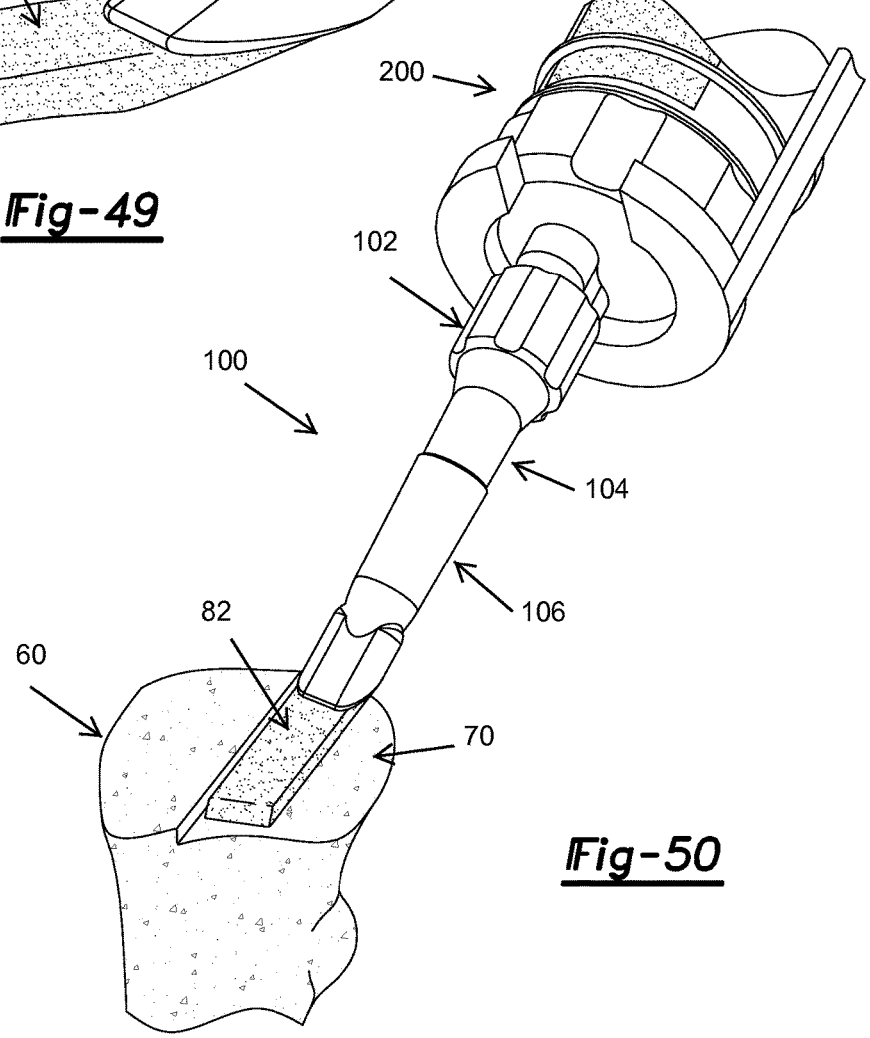
Figure 51:
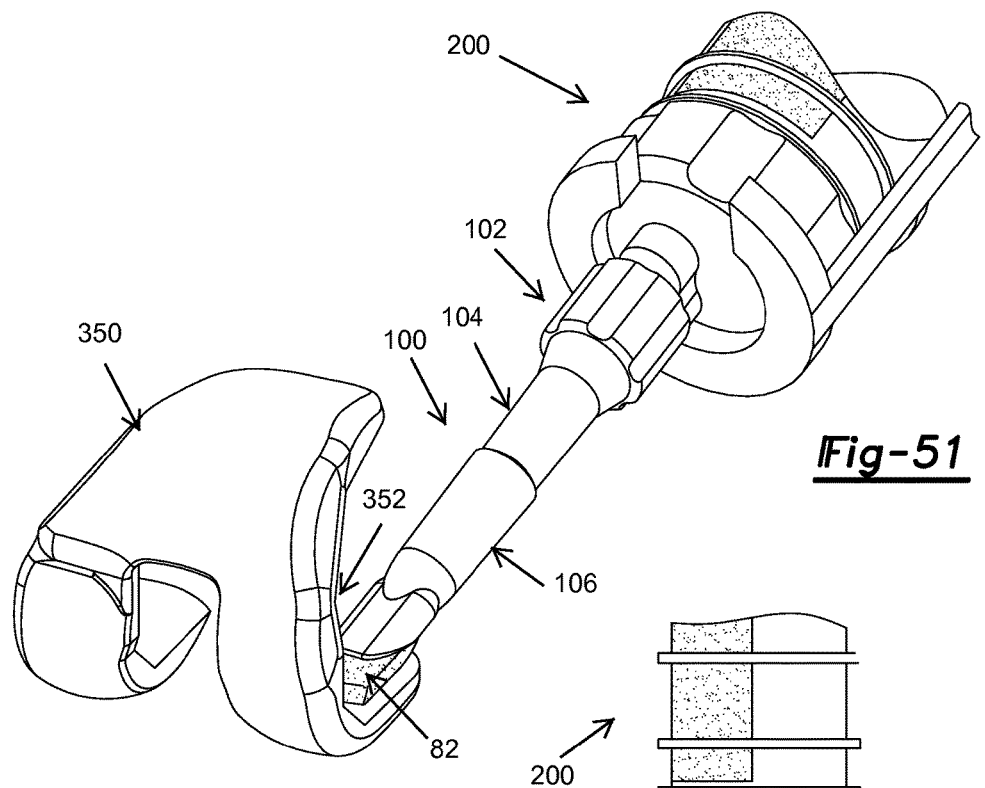
Figure 52:
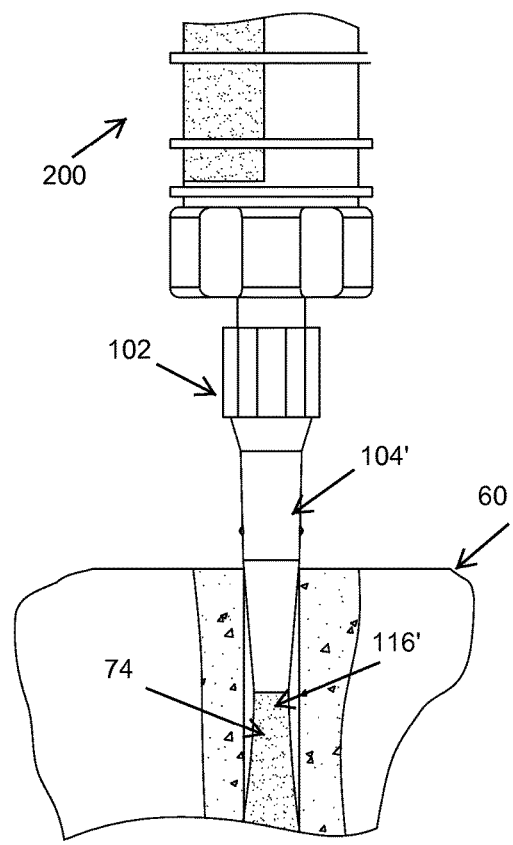

FIG. 9 a rear end view of the bone cement nozzle and alternative nozzle augment of FIG. 8;

FIG. 10 is a sectional view of the alternative nozzle augment and bone cement nozzle of FIG. 8;

FIG. 11A depicts the nozzle augment of FIG. 2 accessing a space between a tibia and a femur;

FIG. 11B depicts the alternative nozzle augment of FIG. 8 accessing the space between the tibia and the femur;

FIG. 12 is a top view of the alternative nozzle augment of FIG. 8;

FIG. 13 is a side view of the alternative nozzle augment of FIG. 8;

FIG. 14 is a bottom view of the alternative nozzle augment of FIG. 8;

FIG. 15 is a perspective view of an alternative bone cement nozzle according to the present teachings;

FIG. 16 is a side view of the alternative bone cement nozzle of FIG. 15;

FIG. 17 is a read end view of the alternative bone cement nozzle of FIG. 15;

FIG. 18 is a side cross-sectional view of the alternative bone cement nozzle of FIG. 15;

FIG. 19 is a perspective view of an alternative bone cement nozzle including an attachment groove according to the present teachings;

FIG. 20 is a perspective view of an alternative nozzle augment including an attachmentsystem attached to the alternative bone cement nozzle of FIG. 19;

FIG. 21 is a rear end view of the alternative bone cement nozzle and alternative nozzle augment of FIG. 20;

FIG. 22 is a side cross-sectional view of the alternative nozzle augment including the clipping system and the alternative bone cement nozzle of FIG. 20;

FIG. 23 is a top view of the alternative nozzle augment including the attachment system of FIG. 20;

FIG. 24 is a side view of the alternative nozzle augment including the attchment system of FIG. 20;

FIG. 25 is a bottom view of the alternative nozzle augment including the clipping system of FIG. 20;

FIG. 26 is a perspective view of an alternative nozzle augment including an oblong stop system attached to the alternative bone nozzle of FIG. 19;

FIG. 27 is a rear end view of the alternative bone cement nozzle including the alternative nozzle augment and oblong stop system of FIG. 26;

FIG. 28 is a side cross-sectional view of the alternative nozzle augment including the oblong stop system attached to the alternative bone nozzle of FIG. 26;

FIG. 29 is a top view of the alternative nozzle augment including the oblong stop system of FIG. 26;

FIG. 30 is a side view of the alternative nozzle augment including the oblong stop system of FIG. 26;

FIG. 31 is a bottom view of the alternative nozzle augment including the oblong stop system of FIG. 26;

FIG. 32 is a perspective view of an alternative tapered bone cement nozzle according to the present teachings;

FIG. 33 is a perspective view of an alternative nozzle augment including a tapered portion attached to the alternative tapered bone cement nozzle of FIG. 32;

FIG. 34 is a rear end view of the alternative nozzle augment including tapered portion attached to the alternative tapered bone cement nozzle of FIG. 33;

FIG. 35 is a side cross-sectional view of the alternative nozzle augment including tapered portion attached to the alternative tapered bone cement nozzle of FIG. 33;

FIG. 36 is a top view of the alternative nozzle augment including the tapered portion of FIG. 33;

FIG. 37 is a side view of the alternative nozzle augment including the tapered portion of FIG. 33;

FIG. 38 is a bottom view of the alternative nozzle augment including the tapered portion of FIG. 33;

FIG. 39 is a perspective view of an alternative nozzle augment including a plurality of oblong shapes attached to an alternative bone cement nozzle including a plurality of stops according to the present teachings;

FIG. 40 is a rear end view of the alternative nozzle augment and alternative bone cement nozzle of FIG. 39;

FIG. 41 is side cross-sectional view of the alternative nozzle augment and alternative bone cement nozzle of FIG. 39;

FIG. 42 is a side view of the alternative nozzle augment and alternative bone cement nozzle of FIG. 39;

FIG. 43 is a top view of the alternative nozzle augment and alternative bone cement nozzle of FIG. 39;

FIG. 44 is an alternative side view of the alternative nozzle augment and alternative bone cement nozzle of FIG. 39;

FIG. 45 is a bottom view of the alternative nozzle augment and alternative bone cement nozzle of FIG. 39;

FIG. 46 is a sectional view of the top view of the alternative nozzle augment and alternative bone cement nozzle of FIG. 44;

FIG. 47 is a perspective view of the nozzle augment and bone cement nozzle of FIG. 2 shown attached to a bone cement cartridge;

FIG. 48 is a perspective view of the nozzle augment and bone cement nozzle and cartridge of FIG. 47 loaded to a bone cement gun;

FIG. 49 is a perspective view of a nozzle augment and a bone cement nozzle according to the present teachings showing delivery of a flat strip of bone cement;

FIG. 50 is a perspective environmental view of a nozzle augment and a bone cement nozzle according to the present teachings showing an application of flat strips of bone cement to a tibial bone surface in preparation for a knee implant;

FIG. 51 is a perspective environmental view of a nozzle augment and a bone cement nozzle according to the present teachings showing an application of flat strips of bone cement to a femoral knee implant;

FIG. 52 is a perspective environmental view of the bone cement nozzle used for a filling a stem hole in a tibia after the nozzle augment is removed.

Corresponding reference numerals indicate corresponding parts throughout the several views of the drawings.

DETAILED DESCRIPTION

Example embodiments will now be described more fully with reference to the accompanying drawings.

The present teachings provide a bone cement nozzle 100 (see FIG. 1) that can be used with a bone cement applicator 300, such as a bone cement cartridge 200 that can be loaded on an arm 252 of a bone cement gun 250 or other bone cement delivery device, as shown in FIG. 48. The bone cement gun 250 shown in FIG. 48 is operated with a pump-type trigger action using a trigger 254. The bone cement nozzle 100 may also be coupled to any suitable type of bone cement source or bone cement delivery source.

The bone cement nozzle 100 of the present teachings may include a distal nozzle augment 106 (FIG. 2) with a distal end 110 configured to provide flat or substantially planar strips or flat layers of bone cement on a bone surface or on an implant surface in preparation for arthroplasty, such as knee, hip, shoulder, or other joint of a patient. The bone cement nozzle 100 of the present teachings includes a connection portion or mechanism 108 that facilitates selectively attaching and separating the distal nozzle augment 106 from the remainder of the bone cement nozzle 100. Further, the connection portion 108 facilitates selectively reattaching the distal nozzle augment 106 to the remainder of the bone cement nozzle 100. In one example, the connection portion 108 protrudes outward from the proximal nozzle portion 104. It is understood that the connection portion 108 may include a dimple or protrusion.

The distal nozzle augment 106 may include a similar mating connection portion 108 with a rear recess or bore facing away from an interior surface of the distal nozzle augment 106. When the distal nozzle augment 106 is axially slid onto the proximal nozzle portion 104, the connection portion, dimple, or protrusion 108 of the proximal nozzle portion 104 may snap into the recess of the connection portion 108 of the distal nozzle augment 106.

In some implementations, separating the distal nozzle augment 106 from the remainder of the bone cement nozzle 100 exposes a new or second distal end 116 (FIG. 1), or alternatively, distal end 116' (FIG. 52) or a distal portion 408 (FIG. 15), suitable for filling holes and/or providing bone cement in smaller or deeper areas of a bone, such as, for example, an intramedullary canal. In this respect, the bone cement nozzle 100 can provide bone cement in a first shape that is substantially in the form of an elongated cylinder using the distal end 116 or 116', and in a second shape that is in the form of a flat or substantially planar strip or flay layers using the distal nozzle augment 106.

Referring to FIGS. 1-7, the bone cement nozzle 100 of the present teachings provides or defines a channel 101 (illustrated in a rear view of the nozzle 100 in FIG. 3) for delivering bone cement. The bone cement nozzle 100 can include a proximal nozzle portion 104 that includes a proximal portion 102 and a distal nozzle augment 106. The proximal portion 102 can be configured to couple the proximal nozzle portion 104 to a bone cement cartridge 200 and/or generally to a bone cement applicator 300 (FIG. 48). The channel 101 extends through the proximal portion 102, proximal nozzle portion 104, and the distal nozzle portion 106 as illustrated in FIG. 3. For example, the proximal portion 102 can include internal threads or other internal formations 130 or other coupling mechanisms for coupling with a bone cement cartridge or cement source 200. Outer formations 132 of the proximal portion 102 can be configured for manual gripping and rotating the bone cement nozzle 100.

The proximal nozzle portion 104 is an elongated tubular portion with a cross-section that can be either constant along its length or variable or tapered along its length. In some embodiments, the proximal nozzle portion 104 can be a hollow cylinder with an inner wall 105 and with a circular, round or other closed curve cross-section that remains longitudinally constant. The proximal nozzle portion 104 includes a round or circular distal opening 116 for delivering bone cement into holes for pegs or stems of implant components associated with the arthroplasty.

The bone cement nozzle 100 can be provided in different sizes and configurations for different arthroplasty applications. For example, for knee arthroplasty, the proximal nozzle portion 104 can have a length L that is shorter than a similar length for a bone cement nozzle 100 to be used in acetabular or hip arthroplasty procedures.

In other embodiments, the bone cement nozzle 100 may include a proximal nozzle portion 104' (FIGS. 15-18). The proximal nozzle portion 104' can be in the form of a truncated cone with a longitudinally linearly variable or tapered circular cross-section. The proximal nozzle portion 104' includes an attachment location, similar to the connection portion 108 described further below.

The proximal nozzle portion 104' may include a proximal portion 404 and a distal portion 408. The proximal portion 404 may be cylindrical with a substantially constant diameter. The distal portion 408 may form a truncated cone with a longitudinally linearly variable or tapered circular cross-section. In this manner, the proximal nozzle portion 104' tapers from a first diameter 412 to a second diameter 416 as illustrated in FIG. 17. For example only, the second diameter 416 may be between 7 and 9 millimeters, however, any suitable diameter is contemplated by the present teachings.

In some embodiments, the proximal nozzle portion 104' may be attached directly to a bone cement delivery device, such as the gun 300. As illustrated in FIG. 52, the proximal nozzle portion 104' can be used for delivering bone cement into holes for pegs or stems of implant components associated with the arthroplasty. For example, the proximal nozzle portion 104' may deliver bone cement through a distal opening 116' (described in detail below). In some embodiments, the distal opening 116' has a diameter equal to the second diameter 416. In other embodiments, a nozzle augment, such as the distal nozzle augment 106, may be attached to the proximal nozzle portion 104'.

The distal nozzle augment 106 (FIG. 2) includes a proximal portion 107, a connection portion 108, a distal portion 110, and a distal opening 114. The distal nozzle augment 106 can be selectively attached and separated from the proximal nozzle portion 104. Further, the distal nozzle augment 106 can be reattached to the proximal nozzle portion 104 as described above. Accordingly, the same bone cement nozzle 100 can be used to deliver and apply bone cement in either one of two shapes or configurations, i.e., from the oblong distal opening 114 of the distal nozzle augment 106 and/or from a round or circular distal opening 116 of the proximal nozzle portion 104 after the distal nozzle augment 106 is and removed from the bone cement nozzle 100.

The oblong distal opening 114 can be used to deliver flat strips 82 of bone cement 80 (FIG. 49) for covering bone or implant surfaces. The circular distal opening 116 has a diameter D that is smaller than the width W of the oblong distal opening 114 and can be used to deliver bone cement 80 into holes in bone, such as stem holes, peg holes, anchoring holes or other openings for implant fixation, as well into intramedullary bone canals or on to small, tight access areas of a bone or implant surface. Alternatively, the bone cement nozzle 100 may include the proximal nozzle portion 104', as described above. When the bone cement nozzle 100 includes the proximal nozzle portion 104', the distal opening 116' has a diameter equal to the second diameter 416. In this respect, a single bone cement nozzle 100 can be used without the need to change nozzles depending on the application.

Figure 4:
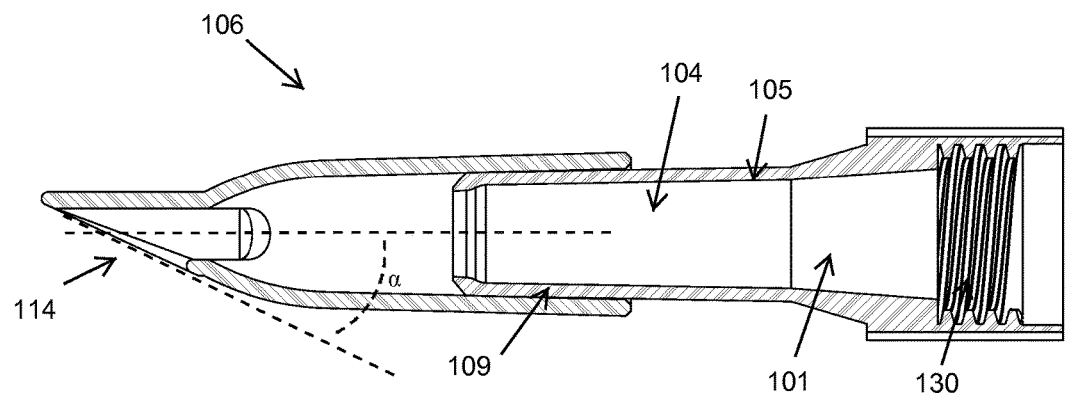
FIG. 4 is a side cross-sectional view of the nozzle augment and bone cement nozzle of FIG. 2.
Figures 5, 6, 7:
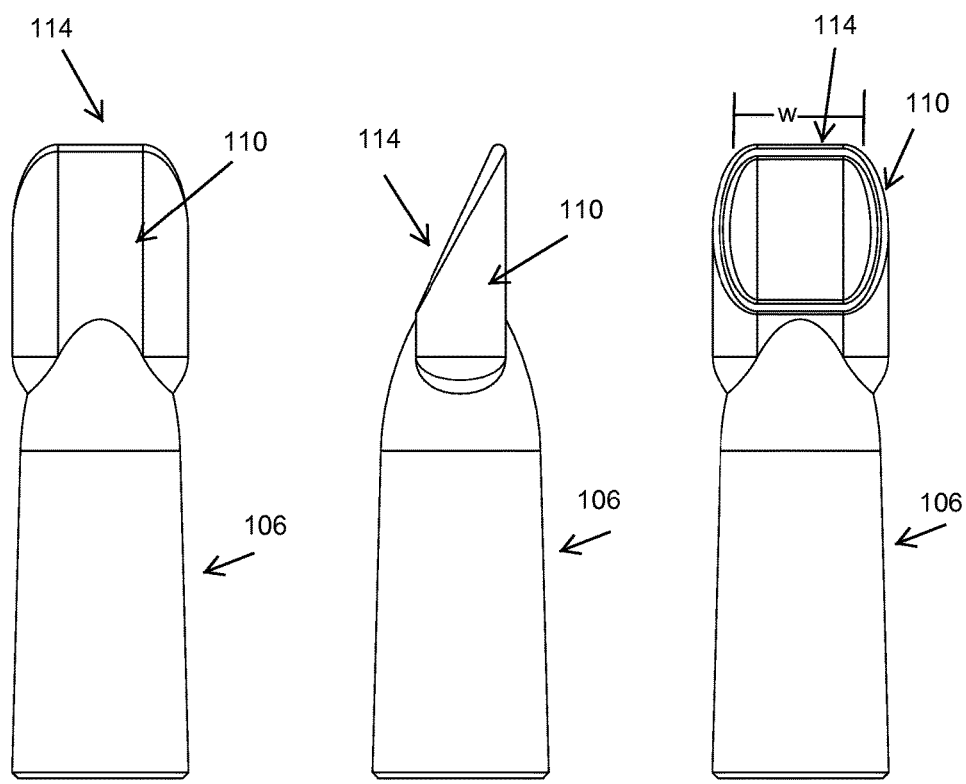
FIG. 5 is a top view of the nozzle augment of FIG. 2.
FIG. 6 is a side view of the nozzle augment of FIG. 2.
FIG. 7 is a bottom view of the nozzle augment of FIG. 2.

In some embodiments, the distal opening 114 may include an angled or slanted portion or tip at angle α as illustrated in FIGS. 4 and 6. The distal nozzle augment 106 may extend along a longitudinal axis. The angled or slanted portion may be at an acute angle relative to the longitudinal axis. For example, he angled portion may be between 20° and 35° or any suitable angle relative to the longitudinal axis. The angled portion α is configured to provide a complete peripheral contact with a bone surface. For example, a surface area of the distal end 110 makes a gapless contact with a bone surface when the distal nozzle augment is laid on the bone surface as illustrated in FIG. 11.

The angled portion α can provide a funnel embedded in distal nozzle augment 106. For example, the distal nozzle augment 106 tapers relative to the distal end 110 as illustrated in FIG. 4. The funnel-like shape distal end 110 acts as a built-in pressurizer that can pressurize the bone cement 80, insuring deeper penetration into the cancellous bone, prior to the bone cement 80 being extruded through the distal opening 114.

Bone cement 80 is then extruded from the distal opening 114 allowing the bone cement to penetrate inside the bone surface. In other words, because the distal end 110 makes a gapless contact with the bone surface, bone cement extruded through the distal opening 114 is forced downward and follows a shape of the distal opening 114. Further, substantially limited bone cement is wasted due to the gapless contact made by the distal end 110.

In another embodiment, the distal nozzle augment 106 may include a flat or clearance portion 118 as illustrated in FIGS. 8-14. The flat portion 118 can be located on a top or upper portion of the distal nozzle augment 106 and can extend from an end of the distal end 110 to at or near a middle portion of the distal nozzle augment 106. As illustrated in FIGS. 8 and 13, the flat portion 118 may extend from the distal end 110 onto the proximal portion 107. The flat portion 118 allows the distal nozzle augment 106 to enter deeper into an incision than a distal nozzle augment 106 without a flat portion 118. A rear view of the nozzle 100 including the distal nozzle augment 106 is illustrated in FIG. 9.

Further, the flat portion 118 allows a surface of the distal nozzle augment 106, for example, to be kept flat against a surface of the bone. By allowing the distal nozzle augment 106 to enter deeper into the incision, the bone cement nozzle 100 may apply bone cement more efficiently and accurately. In other words, a surgeon is allowed more control over placement, volume, and distribution of bone cement as illustrated generally in FIGS. 11A and 11B.

In some embodiments, the distal nozzle augment 106 may be attached to the proximal nozzle portion 104 and/or 104' via a taper assembly 109 as illustrated in FIG. 4. The taper assembly 109 may include a Morse Taper. For example, an external portion of proximal nozzle portion 104 may slightly taper toward the distal end 116 of the proximal nozzle portion 104. An internal portion of the distal nozzle augment 106 is tapered toward the distal end 110.

The distal nozzle augment 106 will rotate freely about the tapered portion of the proximal nozzle portion 104 when the distal nozzle augment 106 is axially slid into a first positon on the proximal nozzle portion 104. For example, the first position may be a position on the proximal nozzle 104 where the tapered portion of the proximal nozzle portion 104 comprises a smaller diameter than the tapered portion of the distal nozzle augment 106. Further, the distal nozzle augment 106 may be frictionally coupled to the proximal nozzle portion 104 when the distal nozzle augment 106 is axially slid into a second position on the proximal nozzle portion 104.

For example, the second position may be a position on the proximal nozzle portion 104 where the tapered portion of the proximal nozzle portion 104 comprises a diameter that is substantially similar to a diameter of the inner tapered portion of the distal nozzle augment 104. In this manner, the tapered portion of the distal nozzle augment 104 may frictionally engage the tapered portion of the proximal nozzle portion 106.

A surgeon and/or medical technician may align the distal nozzle augment 106 to a desired orientation or alignment while the distal nozzle augment 106 is in the first position. The surgeon may axially slide the distal nozzle augment 106 into the a second position. For example, the surgeon may rotate the distal nozzle augment 106 so the distal end 110 is at 90° relative to a bone surface (i.e., a desired orientation relative to bone surface). The surgeon then pushes the distal nozzle augment 106 into the second position on the proximal nozzle portion 104, thereby slideably coupling the distal nozzle augment 106 to the proximal nozzle portion 104. In this manner, the distal end 110 may be aligned with a relatively flat bone surface. When the distal nozzle augment 106 is slideably coupled onto the proximal nozzle portion 104, the distal nozzle augment 106 is frictionally held in place on the proximal nozzle portion 104 and maintains the surgeon selected orientation relative to the bone.

It is understood the distal nozzle augment 106 and the proximal nozzle portions 104 and 104' can be made of any suitable material. For example only, the distal nozzle augment 106 may be made of plastics such as polyethylene, polypropylene, or copolymers in embodiments where the distal nozzle augment 106 is flexible (described in detail below). Additionally or alternatively, the distal nozzle augment 106 may be made of polyethylene, polypropylene, copolymers, or metal in embodiments where the distal nozzle augment 106 is rigid (described in detail below). Further, the proximal nozzle portions 104 and 104' may be made of polyethylene, polypropylene, or copolymers in embodiments where the proximal nozzle portion 104 and/or 104' are flexible (described in detail below). Additionally or alternatively, the proximal nozzle portions 104 and 104' may be made of polyethylene, polypropylene, copolymers, or metal in embodiments where the proximal nozzle portion 104 and/or 104' are rigid (described in detail below).

With reference to FIGS. 19-25, the bone cement nozzle 100 may include an alternative connection assembly such as a clip and groove system. For example, the intermediate nozzle augment 104 and/or 104' may include an annular groove 502. The groove 502 may be disposed near a distal end of the proximal nozzle portion 104 near the proximal portion 102. The groove 502 may be a cutout portion that forms a ring around the proximal nozzle portion 104 as illustrated in FIG. 19. It is understood the groove 502 may only form a partial ring around the proximal nozzle portion 104.

The distal nozzle augment 106 may include a proximal portion 504 and a distal portion 508. The proximal portion 504 includes a plurality of flexible resilient clipping or attaching fingers 512. For example, the proximal portion 504 may include 1, 2, or any suitable number of flexible resilient clipping fingers 512. In one example, the proximal portion 504 includes two flexible resilient clipping fingers 512 on an upper portion of the proximal portion 504 and two flexible resilient clipping fingers on a lower portion of the proximal portion 504. The flexible resilient clipping fingers 512 include a protruding notch configured to snap into the groove 502.

The surgeon assembles the bone cement nozzle 100 by sliding the distal nozzle augment 106 onto the proximal nozzle portion 104 until the protruding notch of the flexible resilient clipping fingers 512 snaps into the groove 502. The surgeon rotates the distal nozzle augment 106 to a desired orientation or alignment as described above. The distal nozzle augment 106 may be rotated up to 360°. The proximal nozzle portion 104 may include the taper assembly 109, such as a Morse Taper, as described above.

The distal portion 508 may taper slightly relative to the proximal portion 504. The surgeon slideably couples the distal nozzle augment 106 onto the proximal nozzle portion 104. The Morse Taper and the distal portion 508 prevent the distal nozzle augment 106 from rotating. In other words, once the surgeon slides the distal nozzle augment 106 onto the proximal nozzle portion 104, the desired orientation will be maintained.

With reference to FIGS. 26-31, the bone cement nozzle 100 may include another alternative connection system. For example, the proximal nozzle portion 104 and/or 104' includes a plurality of stops 516. The plurality of stops 516 may protrude outward from the proximal nozzle portion 104. In some embodiments, the proximal nozzle portion 104 includes a stop 516 on an upper portion of the proximal nozzle portion 104 and a stop on a lower portion of the proximal nozzle portion 104. proximal nozzle portion The distal nozzle augment 106 may include a proximal portion 520 and a distal portion 524 as illustrated in FIG. 26. The proximal portion 520 includes a plurality of oblong recesses 528 near a proximal end of the proximal portion 520. For example, the proximal portion 520 includes an oblong recess 528 on an upper portion of the proximal portion 520 and an oblong recess 528 on a lower portion of the proximal portion 520. The proximal portion 520 may also include a plurality of engageable portions 532.

For example, the proximal portion 520 includes an engageable portion 532 on a first side of the proximal portion 520 and an engageable portion 532 on a second side of the proximal portion 520. It is understood that while any combination of oblong recesses 528 and engageable portions 532 are contemplated by the present disclosure, it may be advantageous to align a first and second oblong recesses 528 adjacent to first and second engageable portions 532 as illustrated in FIGS. 29-31.

The surgeon assembles the bone cement nozzle 100. For example, the surgeon engages, presses, or squeezes the engageable portions 532, such that, the engageable portions 532 are brought toward each other. By engaging the engageable portions 532, a portion of the distal nozzle augment 106, near the oblong recess 528, is temporarily deformed providing clearance for the stops 516 to pass under the distal nozzle augment 106 and into the oblong recess 528. The surgeon pushes the distal nozzle augment 106 onto the proximal nozzle portion 104 until the stops 516 are placed within the oblong recesses 528.

The distal nozzle augment 106 may be oriented at 0° or 180°. The surgeon rotates the distal nozzle augment 106 to a desired orientation. The surgeon releases the engageable portions 532. The distal nozzle augment 106 may then rotate from a first side of the oblong recesses 528 to a second side of the oblong recesses 528.

In other words, the distal nozzle augment 106 can be rotated to an angle associated with the stop 516 being at or near the first side of the oblong recess 528 or to an angle associated with the stop 516 being at or near the second side of the oblong recess 528. It is understood that the distal nozzle augment 106 may be rotated to any angle between the angles associated with the stop 516 being at one of the first and second sides of the oblong recess 528. Further, the surgeon may rotate the distal nozzle augment, while engaging the engageable portions 532, so as to place the distal nozzle augment 106 at either 0° or 180° relative to the proximal nozzle portion 104.

The bone nozzle illustrated in FIGS. 26-31 may include a Morse Taper as described above. In other words, a surgeon may rotate the distal nozzle augment 106 relative to the proximal nozzle portion 104 while the distal nozzle augment 106 is in the first position. Once the surgeon axially slides the distal nozzle augment 106 into the second position on the proximal nozzle portion 104, the desired orientation will be maintained.

With reference to FIGS. 32-38, the distal nozzle augment 106 may include a proximal portion 540 and a distal portion 538. The distal portion 538 may include a bump 544. The bump 544 may protrude inward toward an interior portion of the distal nozzle augment 106 creating an internal shoulder. As described above with reference to FIGS. 1-7, the bone nozzle illustrated in FIGS. 32-38 may include a Morse Taper.

The surgeon rotates the distal nozzle augment 106 to a desired orientation or alignment while the distal nozzle augment 106 is in the first position on the proximal nozzle portion 104. The surgeon then slideably couples the distal nozzle augment 106 into the second position of the proximal nozzle portion 104. The shoulder created by the bump 544 is configured so as not to engage an external portion of the proximal nozzle portion 104, such that, the distal nozzle augment 106 is held in place by the Morse Taper, leaving a gap between shoulder created by the bump 544 and the proximal nozzle portion 104.

For example, the shoulder created by the bump 544 makes contact with the external portion of the proximal nozzle portion 104 when the surgeon slides the distal nozzle augment 106 into the second position of the proximal nozzle portion 104. The bump 544 is pushed onto the proximal nozzle portion 104, thereby locking the distal assembly 106 from rotating. It is understood that while FIGS. 32-38 illustrate a flat portion 118 on the distal nozzle augment 106, the principles described herein apply to a distal nozzle augment with or without a flat portion 118.

With reference to FIGS. 39-46 the bone cement nozzle 100 may include a 360° rotatable connection system or attachment mechanism. For example, the bone cement nozzle 100 includes the proximal nozzle portion 104/104' and the distal nozzle augment 106. As described above with reference to FIGS. 26-31, the proximal nozzle portion 104 and/or 104' includes a plurality of stops 516. The plurality of stops 516 may protrude outward from the proximal nozzle portion 104. In some embodiments, the proximal nozzle portion 104 includes a stop 516 on an upper portion of the proximal nozzle portion 104 and a stop on a lower portion of the proximal nozzle portion 104.

The distal nozzle augment 106 may include a proximal portion 550. The proximal portion 550 includes an annular recessed portion 554 near a proximal end of the proximal portion 550. The recessed portion 554 may be a cutout opening that forms a ring 553 at a proximal end of the distal nozzle augment 106. The proximal portion 550 may also include a plurality of flexible finger portions or engageable tabs 532.

For example, the proximal portion 550 includes an engageable tab 532 on a first side of the proximal portion 550 and an engageable tab 532 on a second side of the proximal portion 550 as illustrated in FIGS. 42-46. The proximal portion 550 also includes a plurality of axially extending oblong walls 552. For example, the proximal portion 550 includes a first oblong wall 552 on a first side of the proximal portion 550 and a second oblong wall 552 on a second side of the proximal portion 550. The oblong walls 552 are configured to span the recessed portion 554. Each of the oblong walls 552 are further configured to have an arcuate shape. The arcuate shape of each of the oblong walls 552 are configured to allow the stops 516 to pass beneath the oblong walls 522.

The surgeon assembles the bone cement nozzle 100. For example, the surgeon brings two of the engageable tabs 532 toward each other. By bringing the engageable tabs 532 toward each other, the ring 553 is temporarily deformed allowing the plurality of stops 516 to pass under the ring 553. The surgeon slides the distal nozzle augment 106 onto the proximal nozzle portion 104 until the stops 516 are placed within the oblong recesses 554. As described above, the bone nozzle 100 may include a Morse Taper.

The surgeon releases the engageable tabs 532 placing the distal nozzle augment 106 in the first position on the proximal nozzle portion 104. The surgeon rotates the distal nozzle augment 106 to a desired orientation or alignment as described above. Because the oblong walls 552 allow the stops 516 to pass under the oblong walls 552, the surgeon may rotate the distal nozzle augment 106 up to 360° while stops 516 are placed within the recessed portion 554.

The surgeon axially slides the distal nozzle augment 106 into the second position on the proximal nozzle portion 104, thereby holding the distal nozzle augment 106 in a desired orientation as described above.

It is understood the bone cement nozzle 100 may include a bump, such as the bump 544 described above and illustrated in FIG. 40, which further prevents the distal nozzle augment 106 from rotating once the surgeon slides the distal nozzle augment 106 into the second position on the proximal nozzle portion 104.

Referring to FIGS. 47-52, exemplary methods of using the bone cement nozzle 100 are illustrated. The surgeon, or a member of a surgical team, may select one of the embodiments of the distal nozzle augment 106 described above. The surgeon, or a member of the surgical team, may then select one of the embodiments of the proximal nozzle portion 104 or 104' as described above. Alternatively, in some embodiments, the distal nozzle augment 106 and the proximal nozzle portion 104 are selectively coupled and packaged at a manufacturer's place of assembly. Accordingly, the surgeon, or member of the surgical team, may receive a pre-assembled bone cement nozzle 100.

The surgeon then couples the bone cement nozzle 100 to a bone cement cartridge, such as the cartridge 200 or bone cement source. The cartridge 200 is then placed into a bone cement gun, such as the gun 300. The surgeon then selectively applies bone cement to a surface of a bone. In FIG. 50, for example, the bone cement nozzle 100 is used to apply flat strips, thin flat layers, or ribbons 82 of bone cement on a resected surface 70 of a tibial bone 60 in preparation for receiving a knee tibial implant (not shown). Alternatively, the bone cement can be applied on a flat bone-engaging surface of a tibial tray.

In FIG. 51, the bone cement nozzle 100 is used to apply flat strips 82 of bone cement on an inner, bone-engaging surface 352 of a knee femoral implant in preparation for knee arthroplasty. Similarly, bone cement can be applied directly in the corresponding prepared flat resected surfaces of the distal femoral bone. Accordingly, flat layers of bone cement can be applied and cover flat resected bone without further manipulation of the bone cement, i.e., without having to flatten and spread the delivered bone cement. Each flat layer of bone cement can be terminated or cleanly cut to a desired length by pinching it with the edge of the distal opening 114.

FIG. 52 shows an example of using the distal opening 116 to apply bone cement into a hole 74 prepared on the proximal surface of the tibial bone 60 for receiving a central peg of a tibial implant component (not shown). Bone cement can be similarly delivered into an intramedullary bone canal using the distal opening 116.

Summarizing, the bone cement nozzle 100 of the present teachings can be used to deliver flat layers 82 of bone cement 80 of predetermined width and thickness for covering easily and efficiently a bone surface or a bone engagement surface of an implant component associated with an arthroplasty procedure without further manipulation of the delivered bone cement. The distal nozzle augment 106 of the bone cement nozzle 100 can be easily removed from the proximal nozzle portion 104 by applying enough of a retracting force to overcome the fit of the taper assembly 109 (i.e., the Morse Taper).

Further, the distal nozzle augment 106 may be reattached in any manner described above. Removing the distal nozzle augment 106 exposes a clean circular opening at the distal end 116 of the proximal nozzle portion 104 for delivering bone cement into holes for pegs or stems of implant components associated with the arthroplasty. Additionally, the proximal nozzle portion 104, can be coupled for use with other cementation nozzles, cement preparation nozzle,s or cement pressurizers, such as those provided in commercially available bone cement kits, such as, for example, the Optivac© system and/or the Optipac© system available from Biomet Manufacturing Corp., Warsaw, Indiana, U.S.A.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

In some example embodiments, well-known processes, well-known device structures, and well-known technologies are not described in detail. In this respect, the bone cement nozzle 100 of the present teachings can be provided in a kit including any combination of with bone cement, bone cement cartridge, bone cement mixer, bone cement gun, various bone cementation nozzles for the tibial and or femoral bone, separate bone cement pressurizers, and plugs or seals of various sizes for intramedullary canal applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus for bone cement delivery, comprising:
    a proximal nozzle comprising a proximal end configured to couple to a bone cement source and a first distal delivery end having a circular interior cross section for delivering bone cement having a round cross-sectional shape;
    a distal nozzle comprising a proximal end configured to slideably couple to the first distal delivery end, a second distal delivery end, and a longitudinal axis extending from the proximal end to the second distal delivery end, the second distal delivery end comprising an interior cavity defining a funnel in communication with a delivery tip comprising an oblong interior cross section for delivering flat strips of bone cement, wherein the delivery tip comprises a slanted face disposed at an acute angle between 20 degrees and 35 degrees relative to the longitudinal axis to allow the slanted face to make complete peripheral contact with a bone surface; and
    an attachment mechanism configured to releasably couple the distal nozzle to the proximal nozzle.

2. The apparatus of claim 1, wherein the attachment mechanism comprises a tapered disposed on the proximal nozzle and a tapered disposed on the distal nozzle.

3. The apparatus of claim 2, wherein distal nozzle is selectively rotatable relative to the proximal nozzle when the distal nozzle is axially slid into a first position on the proximal nozzle and wherein the distal nozzle is fixedly coupled to the proximal nozzle when the distal nozzle is axially slid into a second position on the proximal nozzle.

4. The apparatus of claim 1, wherein the attachment mechanism comprises at least one protrusion extending outwardly from the proximal nozzle and:
    at least one oblong recess defined near a proximal end of the distal nozzle, the oblong recess comprising a first side and a second side; and
    one or more engageable tabs disposed at the proximal end of the distal nozzle.

5. The apparatus of claim 4, wherein the distal nozzle is deformable, by engaging the one or more engageable tabs, to allow the at least one protrusion to pass under the proximal end of the distal nozzle and to snap into the at least one oblong recess between the first side and the second side.

6. The apparatus of claim 1, wherein the attachment mechanism comprises at least one flexible resilient finger disposed at a proximal end of the distal nozzle and the proximal nozzle comprises a groove disposed near the proximal end of the proximal nozzle.

7. The apparatus of claim 6, wherein the attachment mechanism is configured to couple the distal nozzle to the proximal nozzle by rotating the distal nozzle to a desired orientation and axially sliding the distal nozzle onto the proximal nozzle until the at least one flexing resilient finger snaps into the groove.

8. The apparatus of claim 1, wherein the attachment mechanism comprises at least one protrusion that protrudes outward from the proximal nozzle and:

an annular recess that defines a ring around the distal nozzle near a proximal end of the distal nozzle;

at least one oblong wall that spans the recess, the at least one oblong wall comprising an arcuate shaped facing the recess, the arcuate portion shaped being configured to allow the at least one protrusion to pass beneath the at least one oblong wall; and at least one engageable tab disposed at a proximal end of the distal nozzle.

9. The apparatus of claim 8, wherein the attachment mechanism is configured to couple the distal nozzle to the proximal nozzle by temporarily deforming the ring by flexing the at least one engageable tab, wherein the distal nozzle is axially slid onto the proximal nozzle such that the at least one protrusion passes beneath the ring and is placed within the recess.

10. The apparatus of claim 1, wherein the proximal end of the distal nozzle comprises a clearance disposed opposite the slanted surface, the clearance being configured to allow the distal nozzle to clear a bone surface opposite the second distal delivery end.

11. An apparatus for bone cement delivery, comprising:
a proximal nozzle extending along a first longitudinal axis and comprising a proximal end configured to couple to a bone cement source and a first distal delivery end comprising a circular interior cross section perpendicular to the first longitudinal axis for delivering bone cement having a round cross-sectional shape;

a distal nozzle extending along a second longitudinal axis and comprising a proximal end configured to slideably couple to the first distal delivery end and a second distal delivery end comprising an interior cavity defining a funnel in communication with a delivery tip comprising an oblong cross section for delivering flat strips of bone cement, the delivery tip comprising a slanted face disposed at an acute angle relative to the second longitudinal axis;

a clearance disposed in the distal nozzle opposite the slanted face, the clearance allowing the distal nozzle to enter a narrow space; and an attachment mechanism configured to releasably couple the distal nozzle to the proximal nozzle.

12. The apparatus of claim 11, wherein the attachment mechanism comprises one of the group consisting of: a Morse Taper; at least one oblong recess defined near a proximal end of the distal nozzle, at least one engageable tab disposed at the proximal end of the distal nozzle, and at least one protrusion protruding outward from the proximal nozzle; at least one annular recess defining a ring near the proximal end of the distal nozzle, at least one engageable tab disposed at the proximal end of the distal nozzle, and at least one protrusion protruding outward from the proximal nozzle; and at least one flexing resilient finger disposed at the proximal end of the distal nozzle and a groove defined on the proximal nozzle.

13. The apparatus of claim 11, wherein the proximal nozzle being configured to couple to a bone cement source includes the proximal nozzle being configured to couple to a bone cement cartridge positioned within a bone cement gun.

14. The apparatus of claim 11, wherein the clearance portion is configured to allow the distal nozzle to clear a bone surface opposite the second distal delivery end and to allow the slanted face to make substantially parallel contact with a delivery surface.

* * * * *

UNITED STATES PATENT AND TRADEMARK OFFICE
CERTIFICATE OF CORRECTION

PATENT NO. : 10,070,907 B2  
APPLICATION NO. : 14/638664  
DATED : September 11, 2018  
INVENTOR(S) : Dupuy et al.

Page 1 of 2

It is certified that error appears in the above-identified patent and that said Letters Patent is hereby corrected as shown below:

On the Title Page

In item (57), in "Abstract", in Column 2, Line 2, after "nozzle", insert --portion--

In item (57), in "Abstract", in Column 2, Line 4, after "nozzle", insert --augment--

In item (57), in "Abstract", in Column 2, Line 8, after "nozzle", insert --augment--

In item (57), in "Abstract", in Column 2, Line 9, delete "nozzle." and insert --nozzle portion.-- therefor In the Claims In Column 12, Line 33, in Claim 2, after "tapered", insert --portion--

In Column 12, Line 34, in Claim 2, after "tapered", insert --portion--

In Column 13, Line 2, in Claim 8, after "nozzle", insert --augment--

In Column 13, Line 4, in Claim 8, after "shaped", insert --portion--

In Column 13, Line 5, in Claim 8, delete "portion shaped" and insert --shaped portion-- therefor In Column 13, Line 18, in Claim 10, after "clearance", insert --portion--

In Column 13, Line 19, in Claim 10, after "clearance", insert --portion--

In Column 14, Line 5, in Claim 11, after "clearance", insert --portion--

In Column 14, Line 6, in Claim 11, after "clearance", insert --portion--  
In Column 14, Line 11, in Claim 12, after "of:", insert --¶--

Signed and Sealed this  
Second Day of April, 2019

Andrei Iancu  
*Director of the United States Patent and Trademark Office*

CERTIFICATE OF CORRECTION (continued)
U.S. Pat. No. 10,070,907 B2

In Column 14, Line 12, in Claim 12, after "Taper;", insert --¶--

In Column 14, Line 16, in Claim 12, after "nozzle;", insert --¶--

In Column 14, Line 20, in Claim 12, after "and", insert --¶--